(12) United States Patent
Duong et al.

(10) Patent No.: US 9,381,055 B2
(45) Date of Patent: Jul. 5, 2016

(54) THERAPEUTIC CRYOABLATION SYSTEM

(71) Applicants: Thach Duong, Tustin, CA (US); Min Frank Zeng, Irvine, CA (US); Peng Liu, Shanghai (CN); Chaohua Xin, Shanghai (CN)

(72) Inventors: Thach Duong, Tustin, CA (US); Min Frank Zeng, Irvine, CA (US); Peng Liu, Shanghai (CN); Chaohua Xin, Shanghai (CN)

(73) Assignee: Cryofocus Medtech (Shanghai) Co. Ltd., Shanghai (CN)

( * ) Notice: Subject to any disclaimer, the term of this patent is extended or adjusted under 35 U.S.C. 154(b) by 229 days.

(21) Appl. No.: 13/942,387

(22) Filed: Jul. 15, 2013

(65) Prior Publication Data

US 2014/0276706 A1    Sep. 18, 2014

Related U.S. Application Data

(63) Continuation-in-part of application No. 13/800,402, filed on Mar. 13, 2013.

(51) Int. Cl.
*A61B 18/02* (2006.01)
*A61B 18/00* (2006.01)

(52) U.S. Cl.
CPC ....... *A61B 18/02* (2013.01); *A61B 2018/00285* (2013.01)

(58) Field of Classification Search
None
See application file for complete search history.

(56) References Cited

U.S. PATENT DOCUMENTS

| | | | |
|---|---|---|---|
| 2003/0060762 A1 | 3/2003 | Zvuloni et al. | 604/113 |
| 2004/0220559 A1* | 11/2004 | Kramer et al. | 606/21 |
| 2007/0167940 A1* | 7/2007 | Stevens-Wright . | A61B 18/1492 606/32 |
| 2010/0280494 A1* | 11/2010 | Matsuura | A61M 25/0021 604/523 |
| 2011/0106074 A1* | 5/2011 | Kunis et al. | 606/41 |
| 2012/0010605 A1* | 1/2012 | Lehmann et al. | 606/23 |
| 2012/0059364 A1* | 3/2012 | Baust et al. | 606/24 |
| 2012/0265186 A1 | 10/2012 | Burger et al. | 606/21 |

FOREIGN PATENT DOCUMENTS

| | | |
|---|---|---|
| CN | 102596119 | 7/2012 |
| CN | 103417288 | 4/2013 |
| WO | WO 2011/017168 | 2/2011 |
| WO | WO 2012/019156 | 2/2012 |

* cited by examiner

*Primary Examiner* — Brian T Gedeon
*Assistant Examiner* — Ankit D Tejani
(74) *Attorney, Agent, or Firm* — Raymond Sun

(57) ABSTRACT

A cryoablation system has a gas source which provides a working nitrogen gas at room temperature and at a constant set pressure, a liquid generator which is coupled to the gas source to receive the working gas, and which then generates a working cryogen fluid, and a catheter coupled to the liquid generator for receiving the working cryogen, the catheter having a distal section having a freezing element which delivers the working cryogen to a treatment location, the catheter also having a balloon positioned adjacent the distal section.

9 Claims, 32 Drawing Sheets

FIG. 18
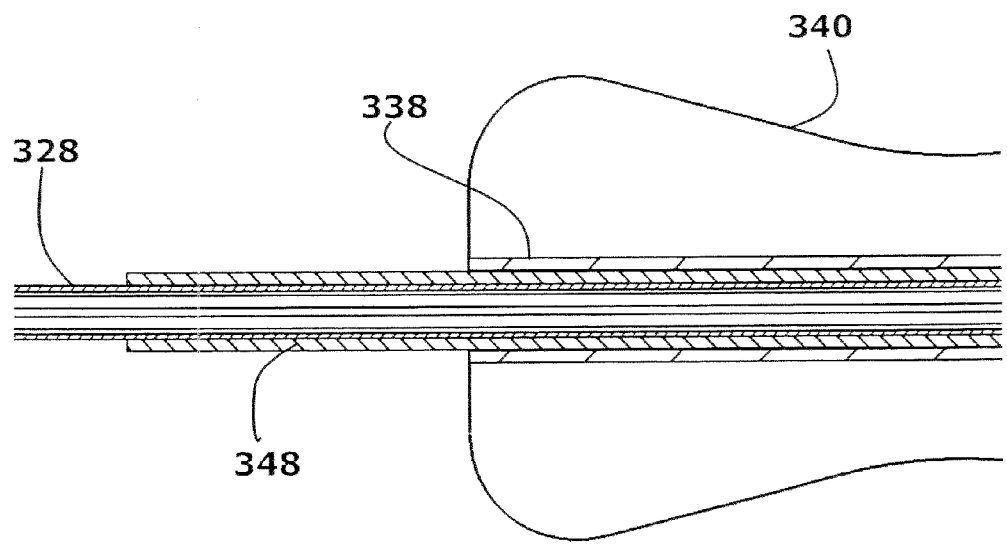
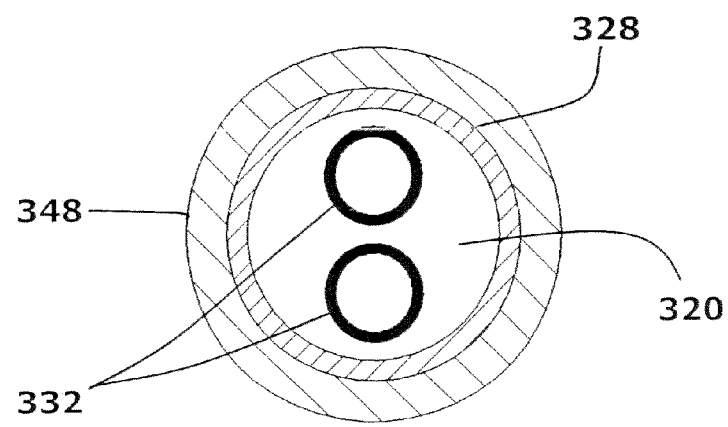
FIG. 19

THERAPEUTIC CRYOABLATION SYSTEM

RELATED CASES

This a continuation-in-part of Ser. No. 13/800,402, filed Mar. 13, 2013.

BACKGROUND OF THE INVENTION

1. Field of the Invention

The present invention relates to a medical device, and in particular, a cryoablation catheter and system for freezing and destroying biological tissues.

2. Description of the Prior Art

Cryosurgical therapy involves the application of extremely low temperature and complex systems designed to suitably freeze the target biological tissue to be treated. Many of these systems use cryoprobes with particular shapes and sizes that are designed to contact a selected portion of the tissue without undesirably effecting adjacent healthy tissues or organs. Extreme freezing is produced with refrigerants that are introduced through a flexible or rigid probe. The freezing is then applied to the target tissue through a thermal transfer element formed as a part of the probe and limited to applying the freezing to a relatively small location.

SUMMARY OF THE DISCLOSURE

It is an object of the present invention to provide an improved cryoablation catheter and system for freezing and destroying biological tissues.

In order to accomplish the objects of the present invention, the present invention provides a cryoablation system having a gas source which provides a working nitrogen gas at room temperature and at a constant set pressure, a liquid generator which is coupled to the gas source to receive the working gas, and which then generates a working cryogen fluid, and a catheter coupled to the liquid generator for receiving the working cryogen, the catheter having a distal section having a freezing element which delivers the working cryogen to a treatment location, the catheter also having a balloon positioned adjacent the distal section.

BRIEF DESCRIPTION OF THE DRAWINGS

FIG. 18 is an enlarged view of the area E in FIG. 16.

FIG. 19 is a cross-sectional view taken along line F-F in FIG. 16.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The Ablation System

Figure 1:
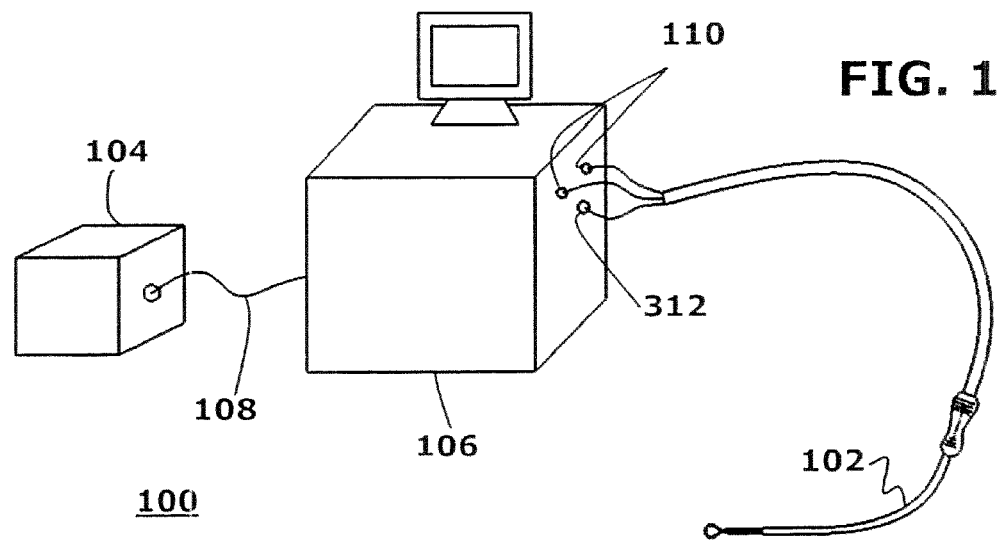
FIG. 1 illustrates a cryoablation system according to the present invention.

Referring to FIG. 1, the present invention provides a cryoablation system 100 that delivers both cold and warm energy to the distal end of a catheter 102 using low-pressure gas, such as nitrogen, helium, argon, neon, etc. The system 100 has a gas source module 104 that supplies working gas to an ablation system 106 through a flexible hose assembly 108. The ablation system 106 receives, directs, transforms, and controls the flow working fluid within the system 100. The ablation system 106 incorporates electrical on/off solenoid valves used to direct gas flow to and from the catheter 102 using computer-controlled software. The ablation system 106 contains a vacuum insulated storage tank/Dewar to store liquid refrigerant which is used to sub-cool the working fluid. The sub-cooled fluid then exits the ablation system 106 through one of two female gas connectors 110. The catheter 102 has two mating interchangeable male gas connectors, where one connector 110 connects and receives the sub-cooled/heated fluid from the ablation system 106. A delivery line positioned within the catheter 102 connects to the female gas connector 110 carrying the working fluid to the distal end of the catheter 102. The working fluid is then circulated back through a loop/manifold into a second delivery line which is positioned parallel to the first delivery line of the catheter 102. The second delivery line connects to the second gas connector 110 at the connector end, and delivers the used fluid from the catheter 102 back into the ablation system 106.

The ablation system also incorporates an active ultra-high vacuum system for thermal insulation purposes. The vacuum system communicates with the catheter vacuum chamber 320 (as described in connection with FIGS. 15, 17, 19, 20, 21 and 24 hereinbelow) via a mechanical vacuum connector 312 and provides a vacuum level to maintain proper thermal insulation to the cryogenic delivery lines against atmospheric heat.

The system 100 of FIG. 1 has built-in mechanical and software safety features to monitor, detect, and control abnormal system responses, as explained in greater detail below.

Figure 2:
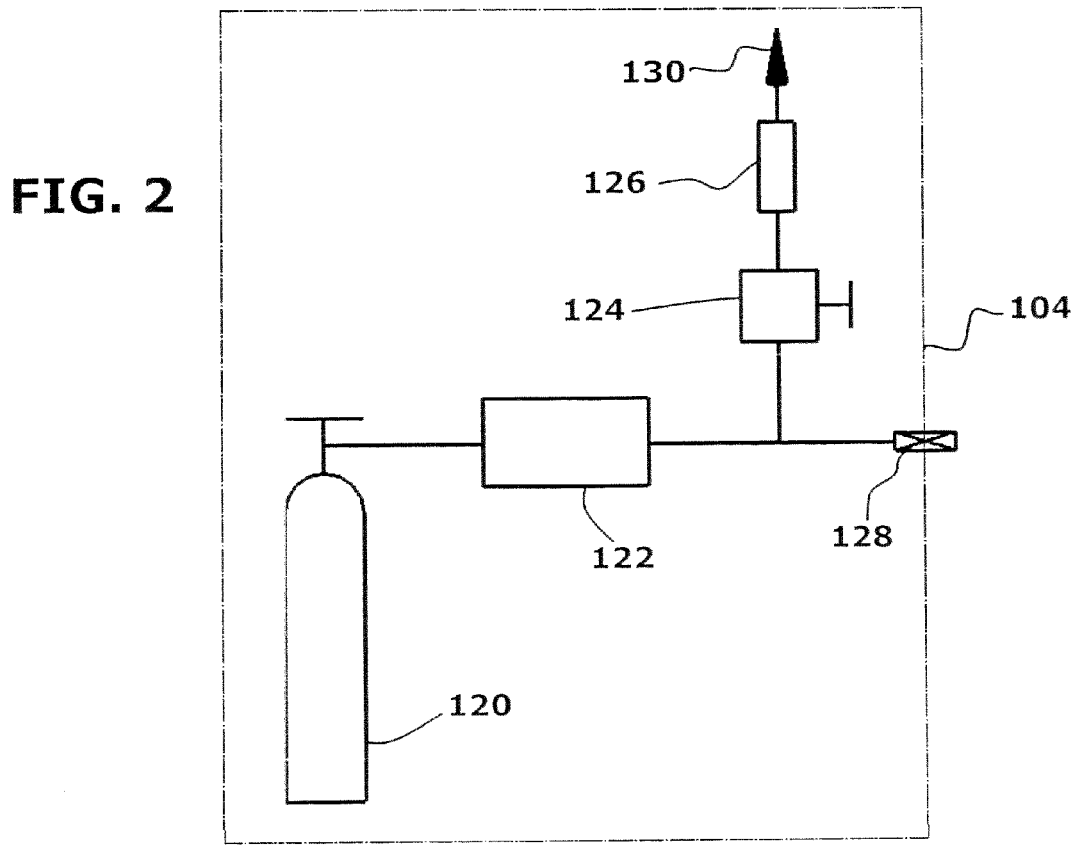
FIG. 2 is a schematic diagram of the gas source module of the system of FIG.

Referring to FIG. 2, the gas source module 104 includes a tank 120 that contains highly compressed nitrogen gas up to approximately 400 atmospheres, a regulator 122 coupled to the tank 120, a manual on/off bleed valve 124, a muffler/silencer 126, and a gas source connector 128. An inline pressure regulator reduces high-pressure gas within a pressure range of approximately 20 atmospheres to 100 atmospheres. An exhaust 130 relieves gas trapped within the pressure line. The gas source connector 128 connects to the outlet of the regulator 122 on one end, and interfaces with the flexible hose assembly 108 at the other end.

Figure 3:
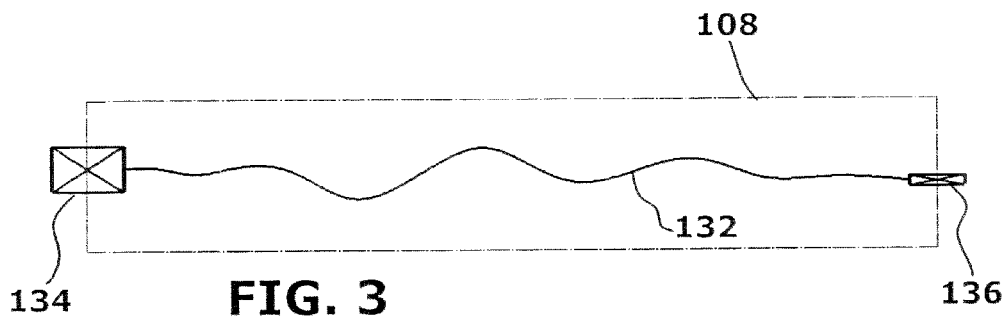
FIG. 3 illustrates the flexible hose assembly of the system of FIG. 1.

The outlet gas from the gas source module 104 is provided to the ablation system 106 through the flexible hose assembly 108. Referring to FIG. 3, the flexible hose assembly 108 has a hose 132 that has a first end that has a female gas connector 134 that has an integrated spring loaded valve. The spring loaded valve opens when mated to a male connector 128 of the gas source module 102. At the second end of the hose 132 is a male gas connector 136 that is connected to the female gas connector 138 at the ablation system 106 (see FIG. 4). Having a male-female connection arrangement prevents gas entrapment between the connector ends if a disconnection occurred while the line is still pressurized.

Regulated gas from the flexible hose assembly 108 will first enter the gas inlet module 140. The outlet of the inlet gas module 140 then splits into two paths to a freeze module 142 and a thaw module 144. The outlets of the freeze module 142 and the thaw module 144 are joined at Point E that leads to one of two female gas connectors 110. The mating male connector of the catheter 102 is connected to this gas connector 110 and receives cryogenic/warm fluid. The other gas connector 110 is connected to a secondary mating connector from the catheter 102, and delivers the used fluid back into the ablation system 106 to pre-cool the inlet gas from the gas source module 104. The system 100 also has a female vacuum connector 112 that communicates with the male vacuum connector at the catheter 102. The two gas connectors 110 are interchangeable, but the vacuum connector 112 is not interchangeable with the gas connectors 110.

Figure 5:
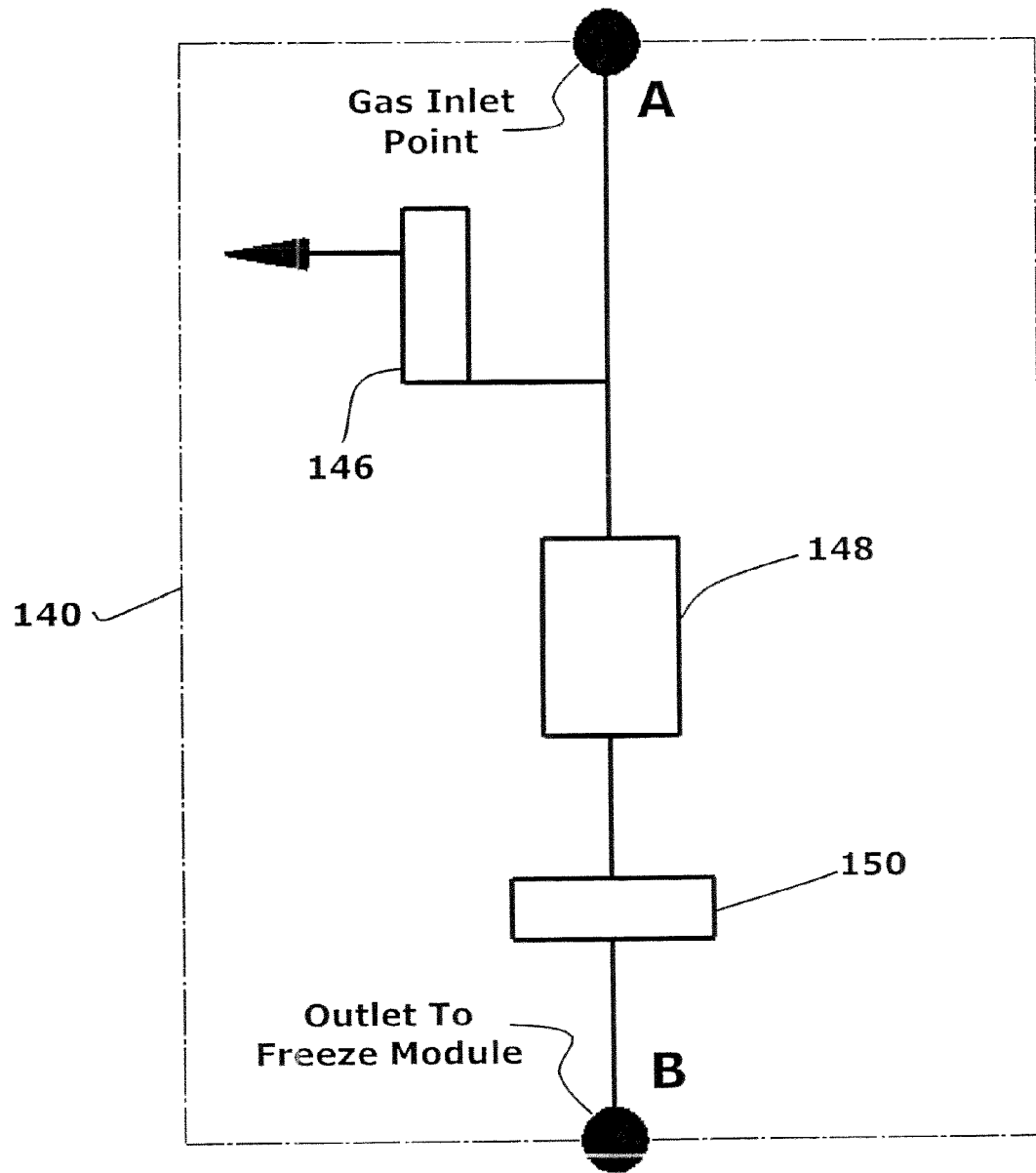
FIG. 5 is a schematic diagram of the gas inlet module of the ablation system of FIG. 4.

Referring to FIG. 5, the function of the gas inlet module 140 is to limit the maximum operating gas pressure, and to control the quality of the working gas. The gas inlet module 140 contains a pressure relief valve 146, a moisture filter 148, and a particle filter 150. The pressure relief valve 146 automatically purges excessive pressure above the set point to prevent over-pressurization. Over-pressurization is usually due to user error in setting the improper regulator pressure at the gas source module 104. The moisture filter 148 and the particle filter 150 trap contaminants that otherwise would migrate and clog the flow passage area. Moisture solidifies as its temperature reduces to zero degrees Celsius, and can therefore block the flow area. Particles can collect and accumulate at small passages, and thereby clog up the flow passage.

Figure 6:
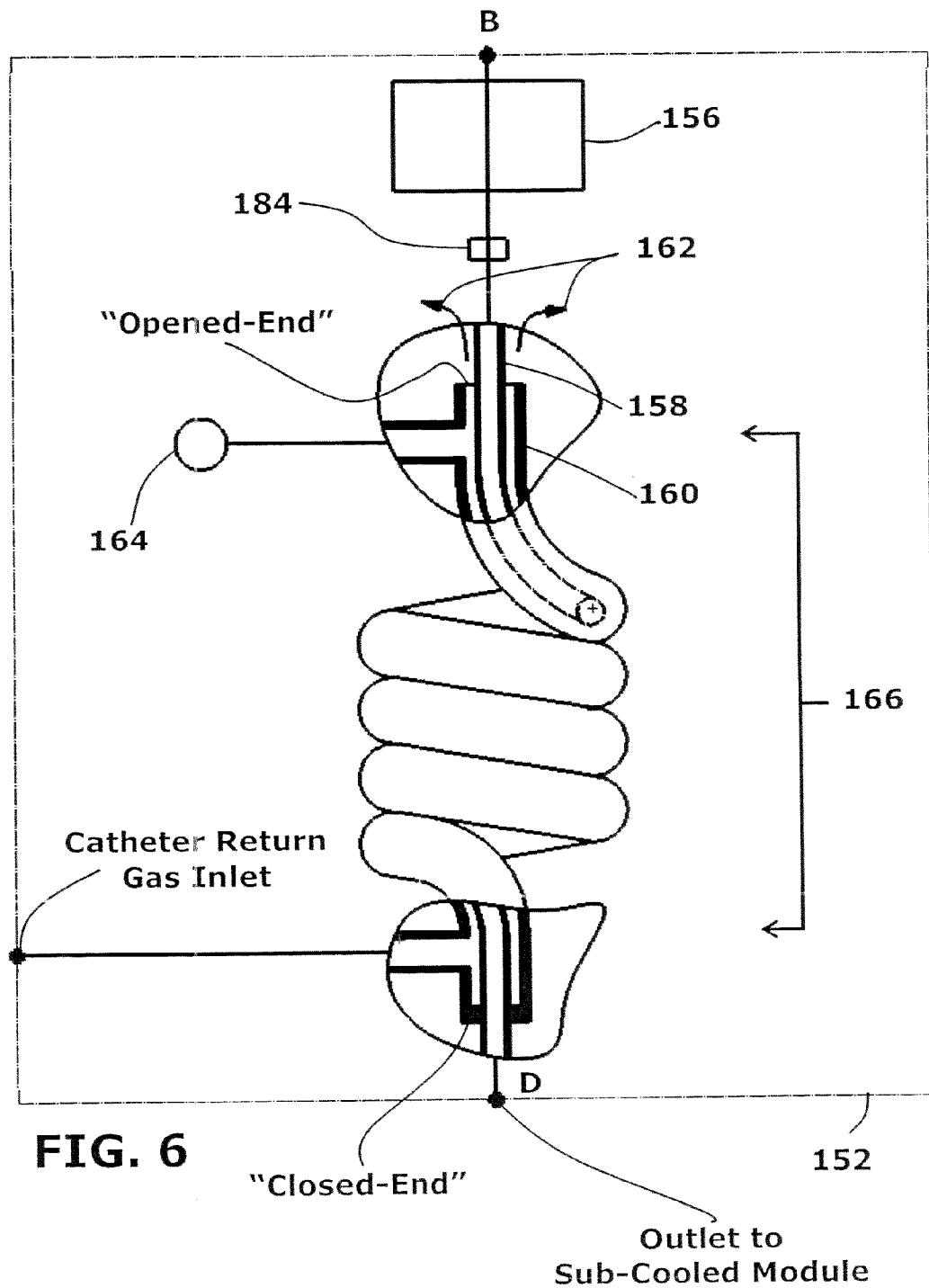
FIG. 6 is a schematic diagram of the first stage pre-cooled module of the ablation system of FIG. 4.
Figure 7:
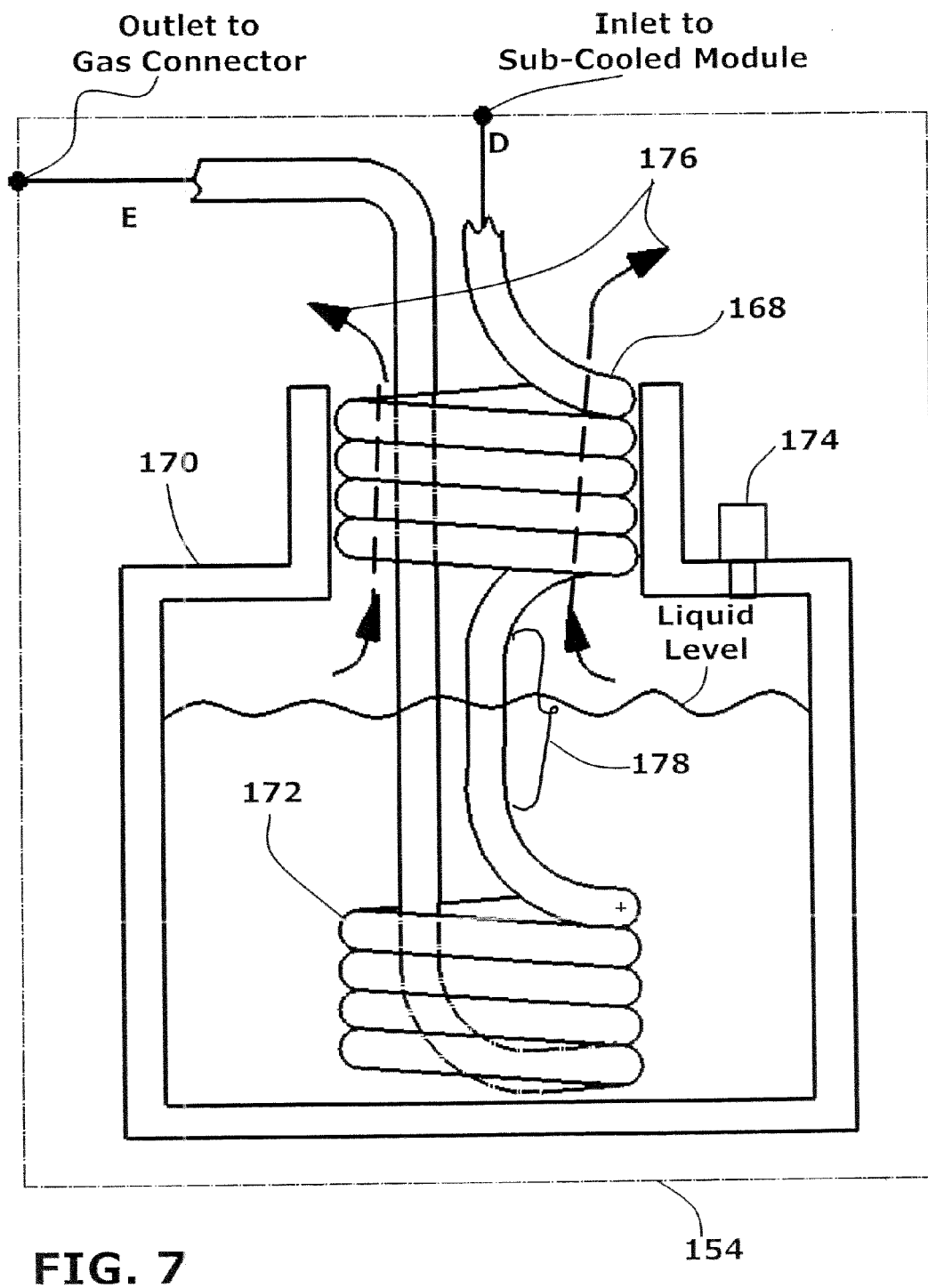
FIG. 7 is a schematic diagram of the sub-cooled module of the ablation system of FIG. 4.

The freeze module 142 contains two sub-modules, a first stage pre-cooled module 152 (see FIG. 6, hereinafter "FSPM")), and a sub-cooled module 154 (see FIG. 7). During the freeze cycle, outlet gas from the inlet gas module 140 feeds into the FSPM 152. Activating a normally closed "Freeze" solenoid valve 156 allows gas to flow into a "tube-in-tube" first-stage heat exchanger 166 that is constructed with two concentric tubes: an inner tube 158 and an outer tube 160. The inner tube 158 carries the working fluid. The space between the inner tube 158 and outer tube 160 carries the return gas 162 from the catheter 102. The gap between the outer tube 160 and inner tube 158 is filled with brazing material forming a pressure tight seal at one end. The gap at the other end of the heat exchanger 166 is opened. The return gas from the catheter 102 enters the heat exchanger 166 starting from Point C in FIGS. 4 and 6, near the closed end of the heat exchanger 166. The return gas 162 then travels counter-flow to the direction of the inlet gas, and exhausts to the atmosphere at The opened end of the heat exchanger 166. The FSPM 152 has an integrated pressure transducer 164 that is positioned near the opened end of the heat exchanger 166. Its function is to monitor the return gas pressure. Information collected from the transducer 164 is used to evaluate system performance and for diagnostic purpose.

With the outlets of the freeze module 142 and thaw module 144 connected to a common gas connector 110, gas can backflow from one module into another module. A check valve 184 (see FIGS. 6 and 8) is incorporated within each module 142 and 144 to prevent this condition. During a freeze or thaw cycle, the respective check valve 184 prevents gas flowing back into the inlet line.

Referring to FIG. 7, pre-cooled gas exiting the FSPM 152 immediately enters a second-stage pre-cooled heat exchanger 168 in the sub-cooled module 154. The second-stage heat exchanger is formed from a single coiled tube. The coil of the heat exchanger 168 is positioned at the neck of a Dewar 170, where vaporized gas converges. The evaporated gas 176 further cools the working fluid as the gas exits the Dewar 170. The working fluid (gas) then exits the coiled section of the second-stage pre-cooled heat exchanger 168 into a straight tube section 178 that is fluidly coupled to the inlet of the sub-cooled heat exchanger 172, which is also formed from a single coiled tube. The sub-cooled heat exchanger 172 is positioned at the bottom of the Dewar 170 where it is submerged within the refrigerant fluid. The working fluid undergoes a phase change to liquid cryogen as it exits the sub-cooled heat exchanger 172. The cryogen is then transported to a female gas connector 110 delivering cryogenic fluid to the catheter 102.

The Dewar 170 is an open storage tank. Evaporated gas is allowed to easily escape before accumulating and building up Dewar pressure. As a secondary safety feature, the Dewar 170 is designed with an integral pressure relief valve 174 to relieve excessive pressure and prevent over-pressurization.

Figure 8:
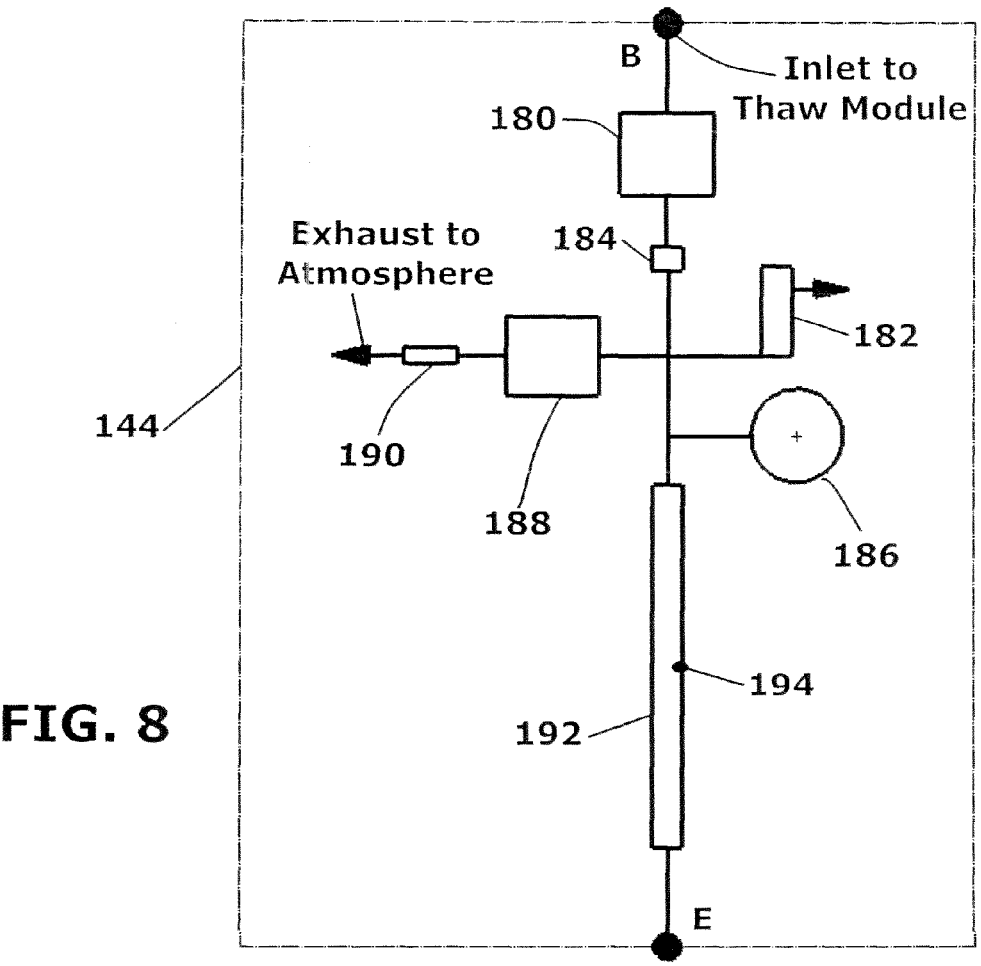
FIG. 8 is a schematic diagram of the thaw module of the ablation system of FIG. 4.

The outlet from inlet gas module 140 can also feed into the thaw module 144 (see FIG. 8). Thawing is desirable at the beginning of a procedure and after a freeze cycle. At the beginning of the procedure, thawing removes residual moisture collected, and flushes the system 100 of contaminants. Residual moisture will clog up the flow passage as it turns to ice, or it can significantly narrow the flow passage, thereby preventing the proper amounts of cryogen from being delivered by the catheter 102 to the ablation region. At the end of the freeze cycle, with the catheter embedded/stuck inside the volume of ice formed during freezing, thawing is required to melt the ice around the catheter 102, allowing the removal or repositioning of the catheter 102. The thawing cycle is started by activating a normally-closed "Thaw" solenoid valve 180, allowing delivery of warm gas into the gas connector 110. System software prevents simultaneous activation of both the "Freeze" valve 156 and the "Thaw" valve 180, as this would cause system inefficiency. The thaw module 144 incorporates a check valve 184, as in the freeze module 142, for the same purpose. A pressure relief valve 182 prevents system over-pressurization, especially when the catheter 102 is connected. In the case of a clogged catheter 102, trapped fluid accumulates heat and causes a rise in pressure as its volume grows. The pressure relief valve 182 automatically purges excessive pressure from the system. As a secondary safety feature, a pressure transducer 186 installed within the delivery line monitors the fluid pressure digitally. This information feeds into the system software. At the detection of an abnormal pressure level, the software will trigger a purge cycle. The purge cycle involves activating a "Purge" solenoid valve 188, and deactivating both the "Freeze" and "Thaw" solenoid valves 156 and 180. Deactivating the "Freeze" and "Thaw" solenoid valves 156 and 180 will stop the gas supply. Activating the "Purge" solenoid valve 188 evacuates all trapped gas in between the fluid lines connecting the "Freeze" to the "Thaw" solenoid valves 156 and 180, with the trapped gas being evacuated to the atmosphere via a silencer 190. Both the Pressure relief valve 182 and pressure transducer 186 sense the inlet fluid pressure to the catheter 102 during both freeze and thaw cycles.

Figure 4:
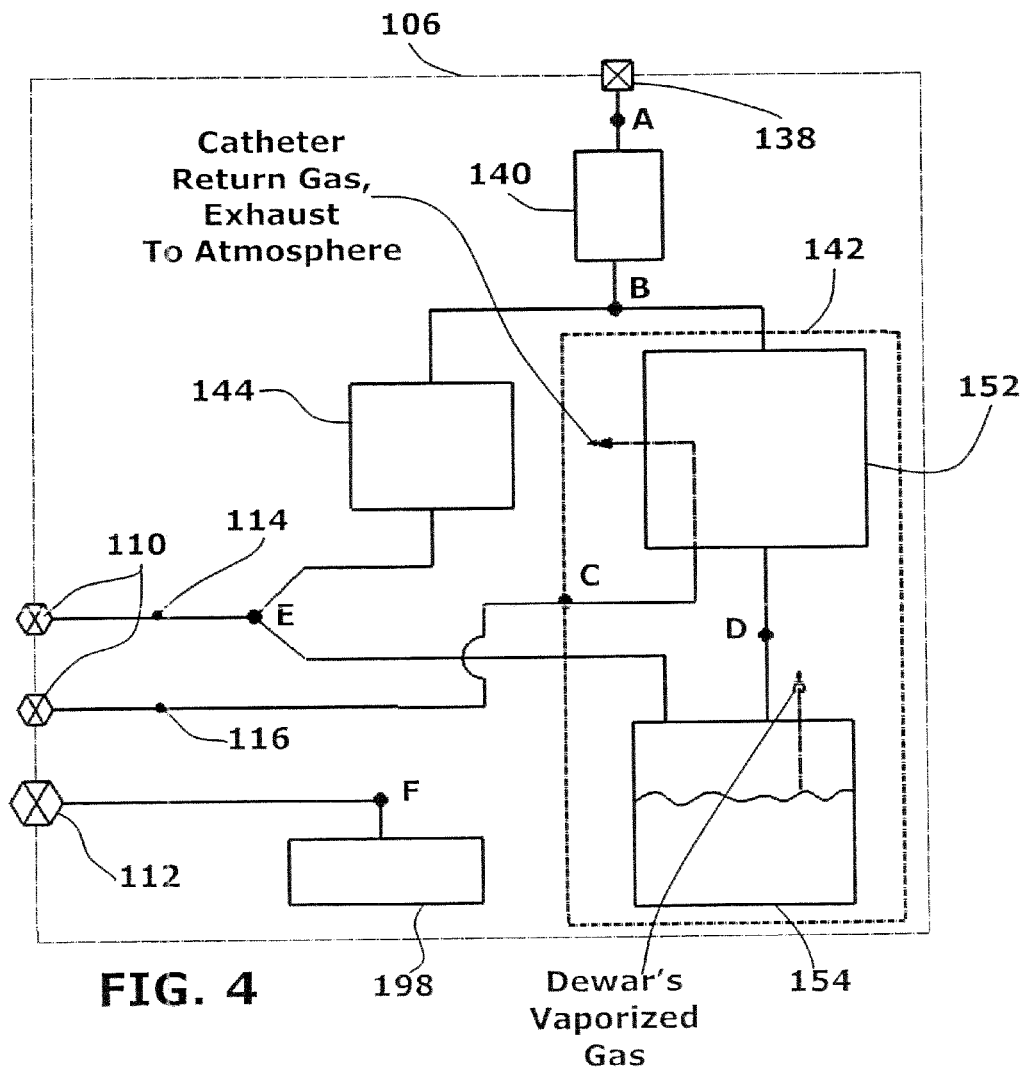
FIG. 4 is a schematic diagram of the ablation system of the system of FIG. 1.

In normal operation, working fluid (gas) enters the thaw module 144 at Point B (see FIGS. 4 and 8), passes through the thaw valve 180 and the check valve 184, and then through an optional in-line heater 192, and then to the gas connector 110 via Point E. Referring to FIG. 4, temperature sensors 114 and 116 are coupled to the gas connectors 110 to sense the temperature of the working fluid (gas).

Figure 9:
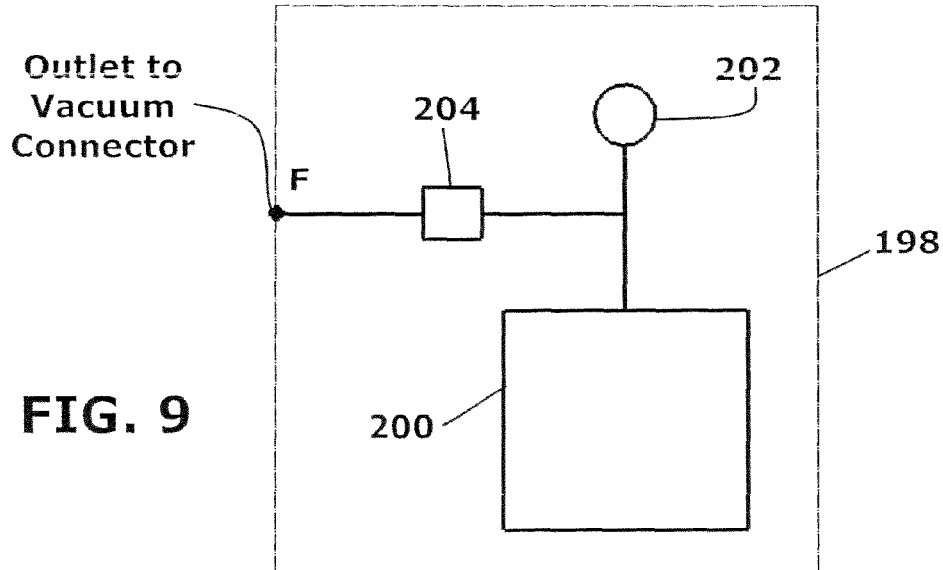
FIG. 9 is a schematic diagram of the vacuum module of the ablation system of FIG. 4.
Figure 10:
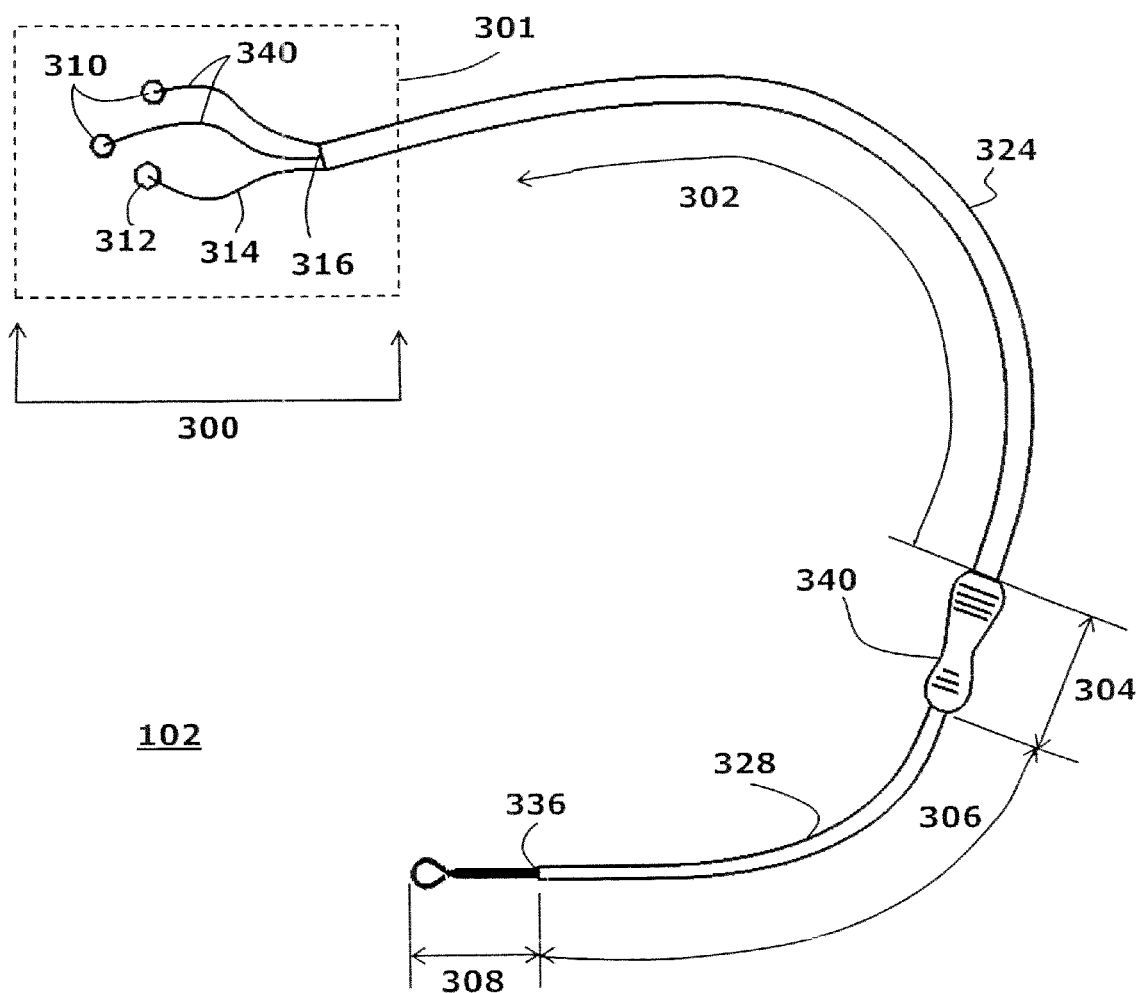
FIG. 10 illustrates the catheter of the system of FIG. 1.

Referring to FIGS. 4 and 9, a vacuum module 198 is also incorporated within the ablation system 106 to provide thermal vacuum insulation to protect the cryogenic fluid from evaporation due to ambient heat. In a perfect vacuum environment, no particles are present to conduct heat from a hot surface to the cold surface. Molecular motion is not available to carry heat from a hot surface to a cold surface either. Therefore, two major modes of heat transfer (i.e., heat conduction and convection) are eliminated. Eliminating the third mode, radiation heat transfer, requires additional shielding. In the present invention, the heat gain from conduction is the most dominant and it is desired to eliminate it.

In practice, it is difficult and impractical to provide a perfect vacuum environment. Fortunately, a perfect vacuum environment is not needed for the present invention. The present invention has two primary objectives. First, it seeks to provide a sufficient level of insulated protection against ambient heat to maintain a certain level of operating efficiency. The present invention attempts to minimize the amount of time taken to deliver cold energy to the distal section 308 of the catheter 102 after activating a freeze cycle. If the catheter 102 not well insulated, the heat gain from the environment along the length of the catheter 102 will result in warm gas being delivered to the distal section 308 of the catheter 102. Second, the present invention seeks to protect the catheter 102 from freezing along the catheter body 306. While the present invention seeks to deliver and focus the cold energy at the distal section of the catheter 102, having cold energy spread along the catheter body 306 not only damages other body tissue, but also reduces the cooling power where needed.

To minimize heat gain by conduction requires a high vacuum level. The vacuum pressure has to be beyond a pressure level where gas conduction becomes dependent on its pressure. In an air-filled environment, the transition pressure from a pressure-dependent to a pressure independent is approximately 10-100 µm Hg. Beyond this pressure point, the thermal conductivity of the gas reduces abruptly. Further reduction in pressure reduces the thermal conductivity of the gas. From experiment in an air-filled environment at standard ambient temperature, it was determined that a vacuum level of 1 µm Hg higher is sufficient for the present invention.

The ablation system 100 employs an active vacuum system in its vacuum module 198, which has a vacuum pump unit 200, a vacuum pressure transducer 202, and a vacuum valve 204. The vacuum pump unit 200 has a two-stage vacuum pump. The first stage is a rough pump that can deliver a vacuum pressure of 10 Torr (1 Torr=1 mm Hg). The second stage, which can be a turbo molecular pump, can deliver a vacuum level of $10^{-8}$ Torr. Both of these pumps works together as a single pump unit. The outlet of the vacuum pump unit 200 splits out to the vacuum pressure transducer 202 and the vacuum valve 204. The vacuum valve 204 can be a normally closed, electrically controlled, on/off solenoid valve. The vacuum valve 204 isolates the vacuum pump unit 200 from the external environment. The pressure transducer 202 senses the vacuum pressure at the inlet of the second-stage vacuum pump, and its digital data is used to synchronize the operations of the two vacuum pumps. The pressure transducer 202 also functions to monitor and detect abnormal pressure level within the catheter vacuum chamber 320 (see FIGS. 15, 17, 19, 20, 21, and 24). Once the vacuum connector 112 is connected to the ablation system 100 and the vacuum valve 204 is activated, the vacuum module 198 and the catheter vacuum chamber 320 will be in communication. Any pressure spike within the catheter vacuum chamber 320 due to leakage from the gas line will be captured by the outer lumen of the catheter 102 and detected by the pressure transducer 202. A shutdown procedure will be triggered by the system software to purge the unwanted gas. The shutdown procedure involves deactivating both the "Freeze" and "Thaw" valves 156 and 180 (as described above), and activating the "purge" and vacuum valves 188 and 204. The vacuum pumps and the vacuum valve 204 remain on or opened unless the vacuum pressure spikes up to set pressure range of 0.01 mm Hg to 1 mm Hg. Once the set pressure is reached, the vacuum valve 204 closes and isolates the vacuum pump unit 200 from the high-pressure source. Exposure of the vacuum system beyond this limit will cause damage. The "purge" valve 138 stays on until the pressure reduces to near atmospheric pressure. At this point, it is safe to remove the catheter 102 and to inspect the catheter 102 and the system 100 for damage.

The vacuum pumps within the vacuum pump unit 200 can operate independently of the catheter 102. Once the catheter 102 is connected to the ablation system 100, activating the vacuum valve 204 will provide communication between the vacuum pump unit 200 and the catheter vacuum chamber 320. Thereafter, the pressure transducer 202 reads the system vacuum pressure. Once the pressure level approaches $10^{-3}$ Torr or 1 µm Hg, the system software then allows the user to perform the freeze cycles.

Overall, the present invention features an open-system where the system 100 receives an external gas source, internally controls and directs the gas source, feeds the gas to a catheter, garnishes the cold energy from the return gas of the catheter, and then exhausts it to the atmosphere. Not reusing or recirculating the used gas makes this system an open-system. The system receives high-pressured gas (e.g., 10 atmospheres to 150 atmospheres) at room temperature. The system refrigerant sub-cools the incoming working fluid (gas). The refrigerant supplied by re-fillable liquid cryogens is stored in a Dewar 170 within the system 100. External gas is converted into liquid cryogen as it passes through a submerged heat exchanger 172 positioned at the bottom of the Dewar 170. Thawing power is supplied by room temperature gas, and or by using an in-line heater 192. The system 100 has built-in safety mechanisms, such as mechanical relief valves 146, 174 and 182, electrical relief valve 18E, particle filter 150, and moisture filter 148. Electrically controlled on/off solenoid valves 156, 180, 188 and 204 are utilized to direct the gas flow. Check valves 184 are incorporated into the system 100 to prevent backflow. A mechanical pressure relief valve 174 is also built into the Dewar 170 to prevent over-pressurization due to vaporization of liquid cryogen. The in-line heater 192 works with a temperature sensor 194 to provide feedback for monitoring and controlling. Temperature and pressure sensors 114, 116 and 164 and 186 are incorporated to monitor both system and catheter performances.

Thus, the system 100 of the present invention provides several important benefits:

i. external gas source (i.e., module 104) supplies the system 100 its working medium n at room temperature and at a constant set pressure within the range of 10 atm to 150 atm.

ii. Inlet gas is sub-cooled by cryogenic fluid stored within the system 100 (i.e., a Dewar tank 170).

iii. The cold return gas from the catheter 102 is used to pre-cool incoming gas.

iv. The system 100 contains an active vacuum pump 198 to provide thermo/vacuum insulation.

vi. The vacuum pump 198 performs a safety function by evacuating any unwanted gas leakage from the catheter 102 that would otherwise migrate into the patient.

vii. The system has an automated leakage monitoring and detection system (i.e., thaw module 144) that has an automated software purge and shutdown procedure to protect the patient.

viii. The system 100 is configured so that thawing of the catheter 102 can be achieved by using room temperature gas, or combined with an in-line heater 192.

The Catheter

Referring to FIG. 10-24, the catheter 102 has a connector section 300, a hose section 302, a proximal section 304, a catheter body 306, and a distal section 308 that functions as an ablation section.

Referring to FIGS. 10 and 22-24, the connector section 300 has two interchangeable gas connectors 310 and a vacuum connector 312. The gas connectors 310 are connected to corresponding gas connectors 110 in the ablation system 100 to receive cold/warm fluid, and to circulate liquid cryogen from the connector end of the catheter 102 to the distal section 308, and then back to the connector end. The vacuum connector 312 is connected to a short vacuum tube 314, which terminates at an air-tight seal 316 located near the hose section 302. The vacuum tube 314 can be made of stainless steel, brass alloy or copper alloy material. The internal opening of the vacuum tube 314 communicates with the catheter vacuum chamber 320 (see FIGS. 15, 17, 19, 20, 21, and 24), which is the chamber or space defined or enclosed by the outer hose 324 and the outer lumen 328, and between the two air-tight seals 316 and 336 located at the connector section 300 and the distal section 308, respectively. The connector section 300 is described as having three separate connectors 310 and 312. However, a single connector assembly 301 can be provided which incorporates and combines all functional features of the three connectors into one.

Figure 16:
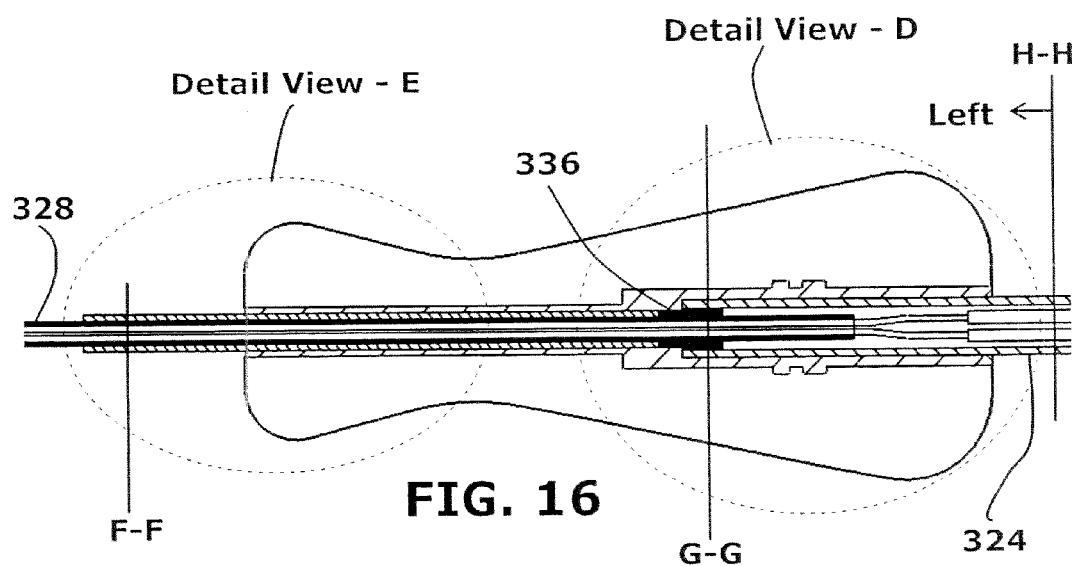
FIG. 16 is a side view of the proximal section of the catheter of FIG. 10.
Figure 17:
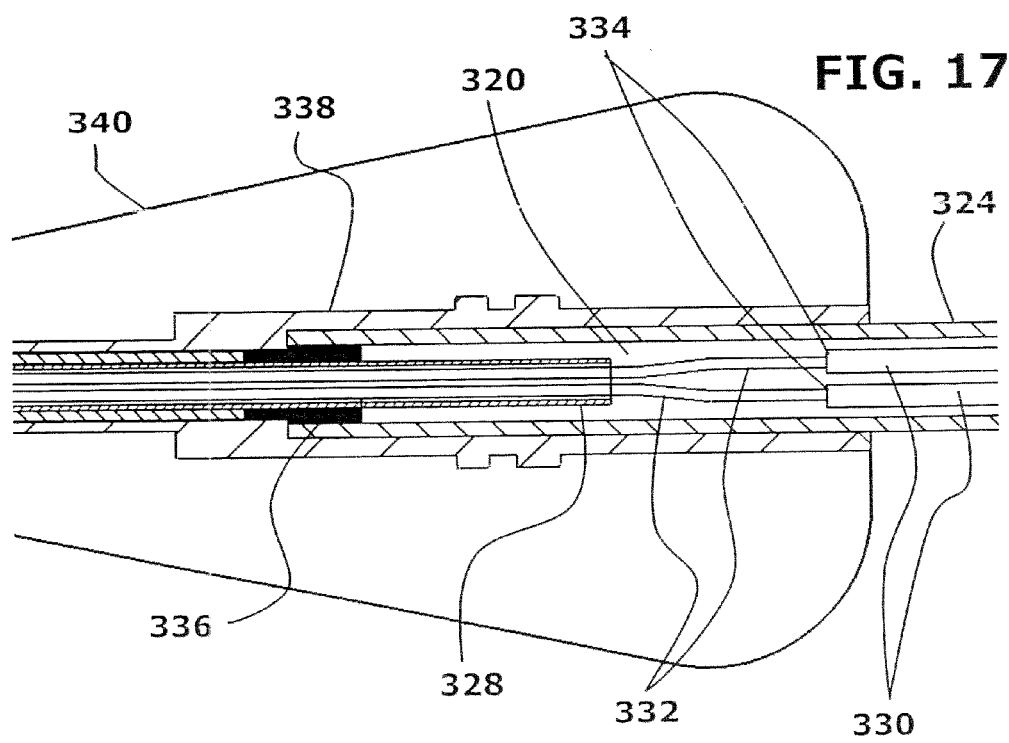
FIG. 17 is an enlarged view of the area D in FIG. 16.
Figure 20:
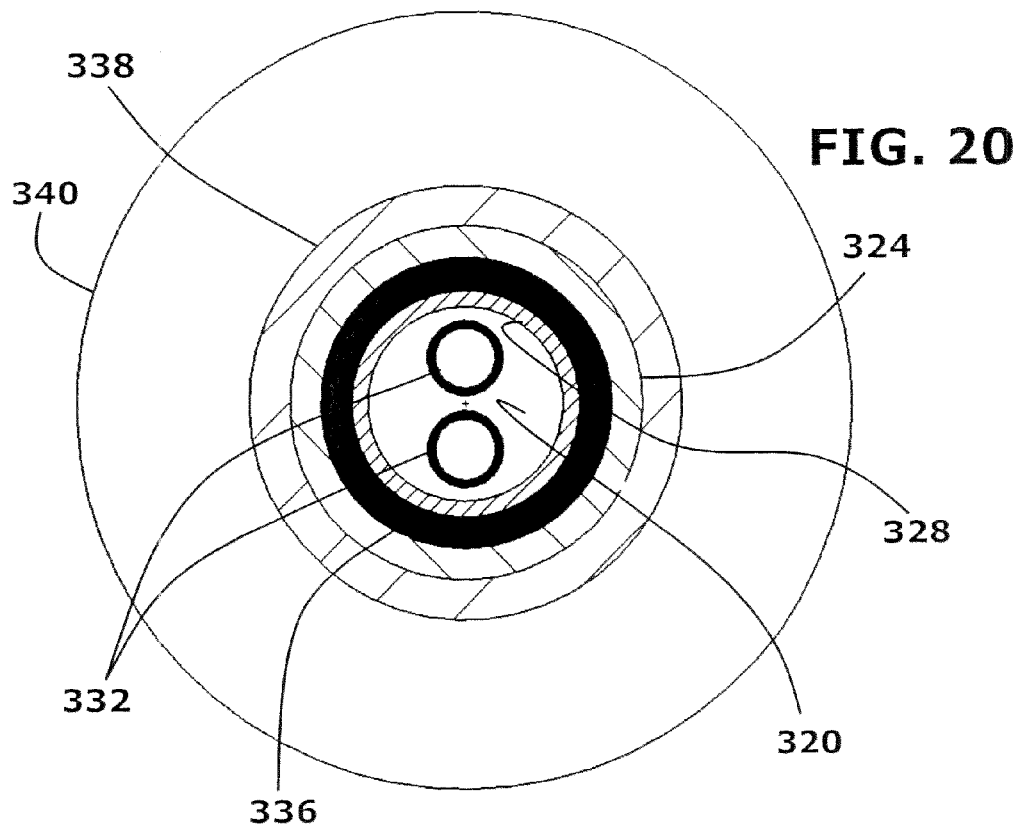
FIG. 20 is a cross-sectional view taken along line G-G in FIG. 16.
Figure 21:
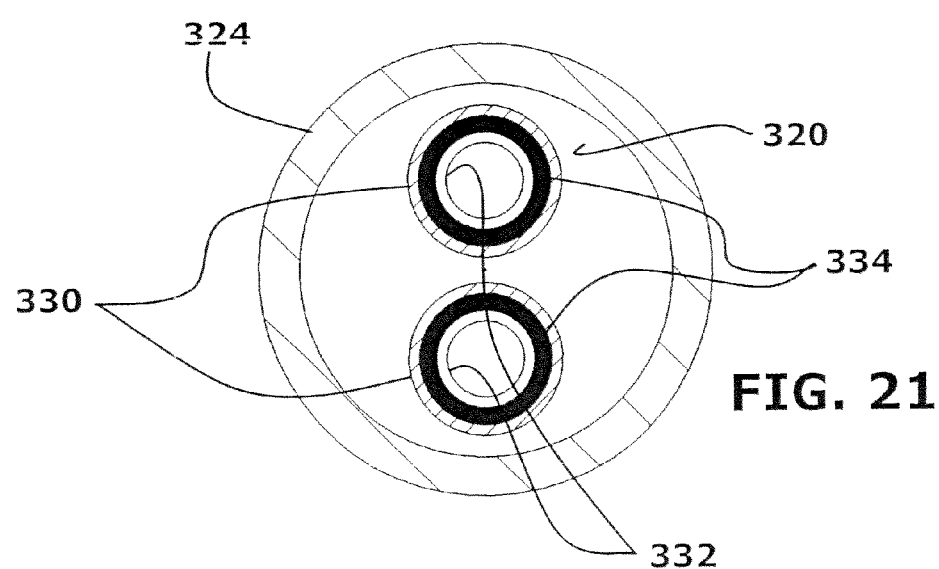
FIG. 21 is a cross-sectional view taken along line H-H in FIG. 16.
Figure 22:
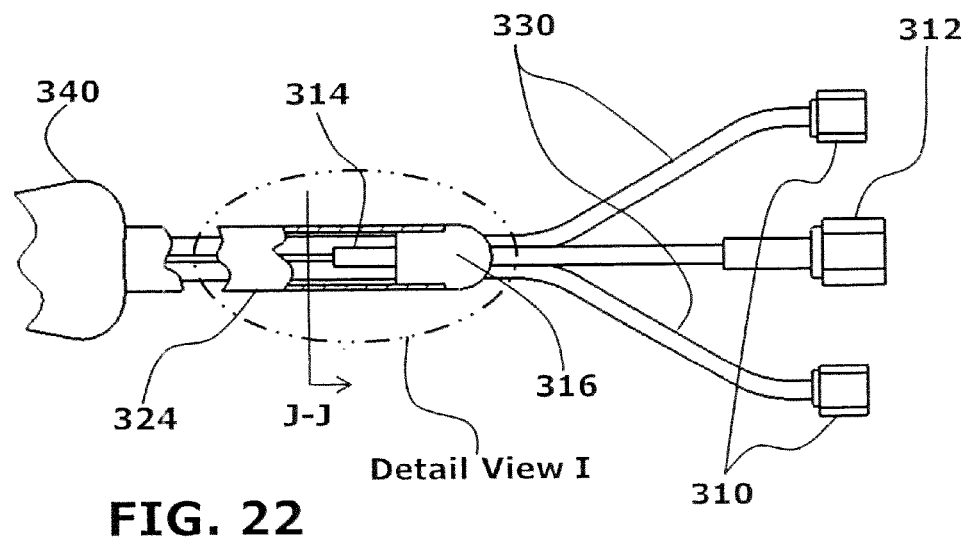
FIG. 22 is a side view of the connector section of the catheter of FIG. 10.
Figure 23:
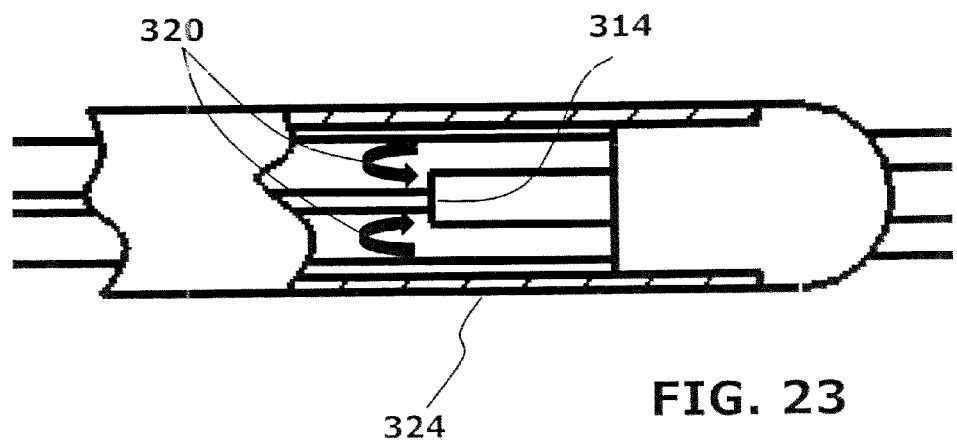
FIG. 23 is an enlarged view of the area I in FIG. 22.
Figure 24:
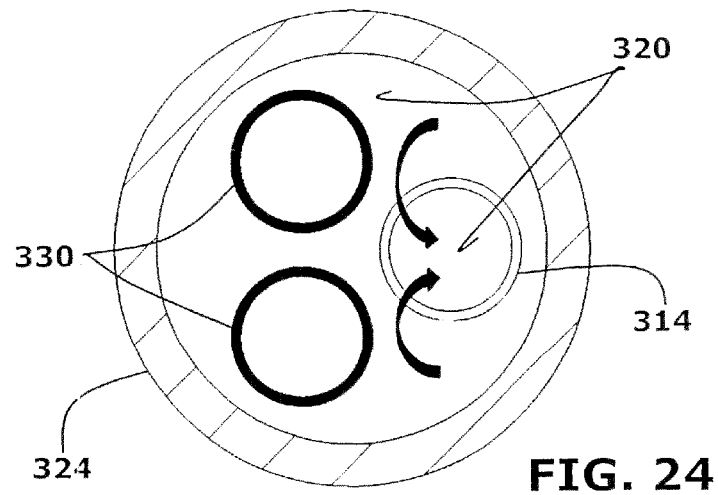
FIG. 24 is a cross-sectional view taken along line J-J in FIG. 22.
Figure 25:
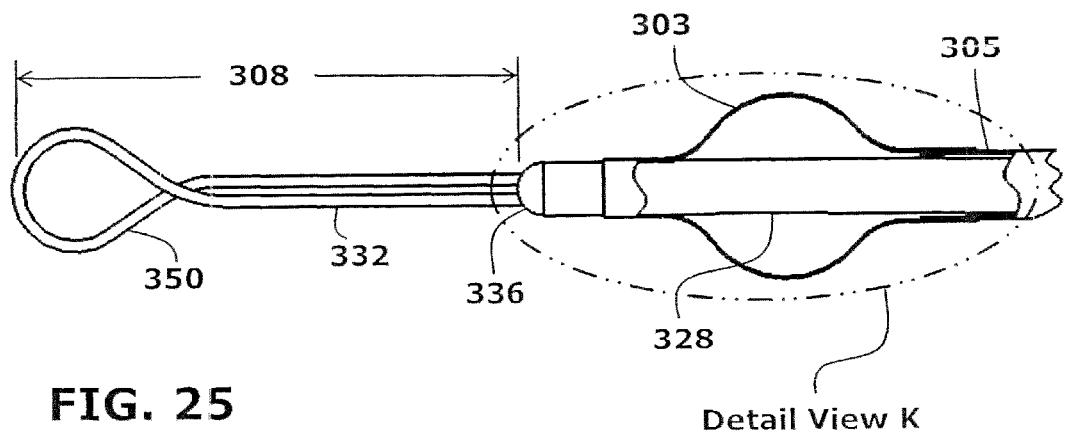
FIG. 25 is a side view of the distal section of another embodiment of the catheter of FIG. 10.
Figure 26:
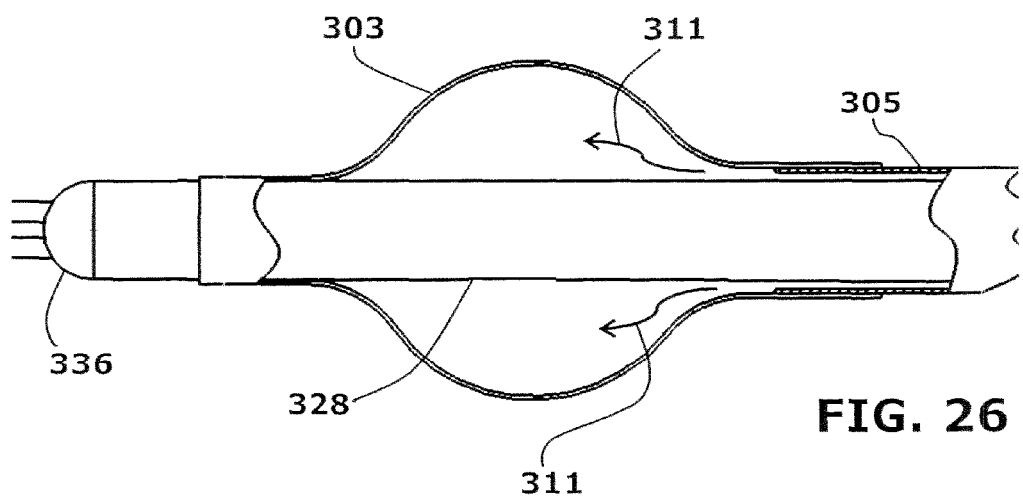
FIG. 26 is an enlarged side view of area K in FIG. 25.
Figure 27:
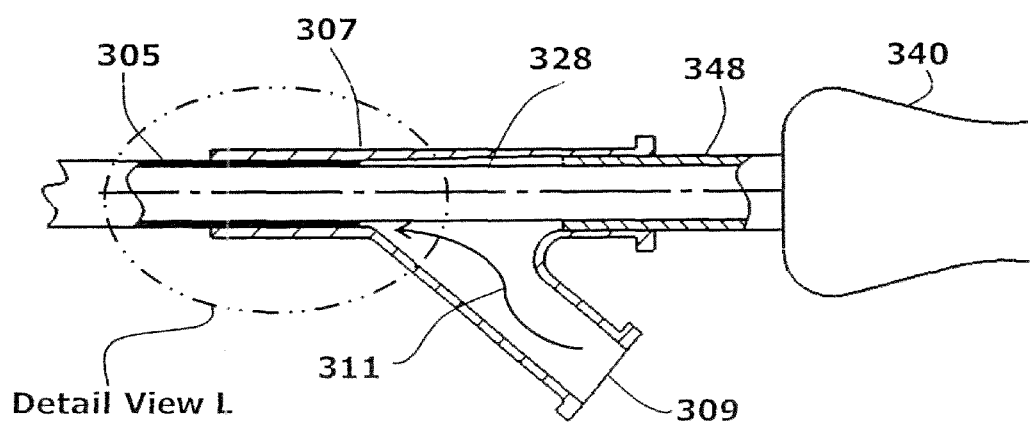
FIG. 27 is an enlarged cross-sectional side view of the proximal portion of the catheter of FIG. 25.
Figure 28:
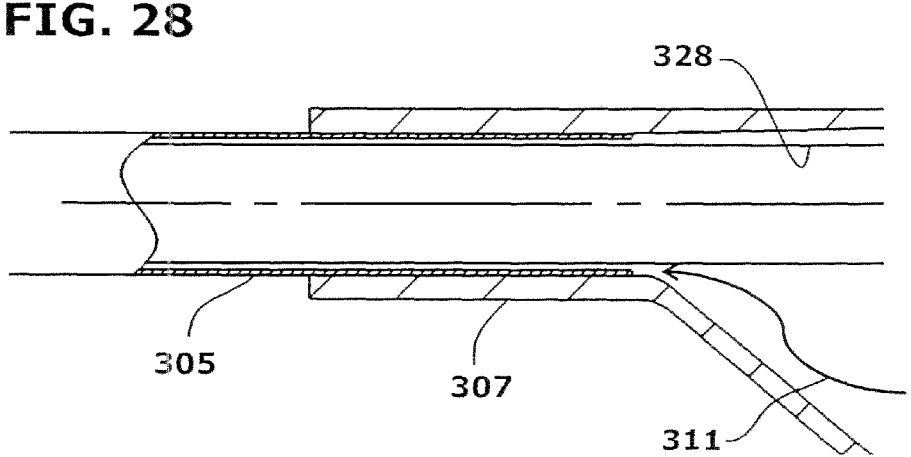
FIG. 28 is an enlarged view of the area L in FIG. 27.

Referring to FIGS. 16, 17 and 21, the hose section 302 is structured with a flexible outer hose 324 made of nylon material or other vacuum rated tubing materials such as PTFE, FEP, Pebax, polyurethane, and polyethene. At the connector section 300, the hose 324 is sealed by epoxy to the two delivery tubes 330 and to the vacuum tube 314. Other sealing methods forming an airtight seal among the flexible outer hose 324, the two delivery tubes 330, and the vacuum tube 314 are possible, such as thermal bonding, using EV cured glue, or a combination thereof. At the proximal section 304, the hose 324 is sealed by epoxy to the outer lumen 328. The epoxy seal can be replaced by thermally bonding the hose 324 to the outer lumen 328, or using EV cured glue, or a combination thereof. The entire length of the hose 324 encapsulates the two delivery tubes 330 that are positioned parallel to each other inside the hose 324. The delivery tubes 330 can be made of brass alloy or copper alloy.

Referring to FIGS. 11 and 14-19, the proximal section 304 of the catheter 102 is where the tubes transition. The larger-diameter stainless steel, brass alloy or copper alloy delivery tubes 330 extending from the connector section 300 are joined with two corresponding smaller-diameter delivery tubes 332, which lead into the smaller-diameter outer lumen 328 at the other end. This is best shown in FIG. 17. The delivery tubes 332 can be made of a stainless steel or copper-nickel alloy. The outer lumen 328 can be a flexible tube made from Pebax material and having a reinforced stainless steel coil or other flexible material without reinforced stainless steel coil, such as Teflon™, FEP (fluorinated ethylene propylene), nylon, PEEK, polyimide, polyurethane, or polyethylene tubing. The outer lumen 328 can also be made by combining different materials such as the ones listed above. In one arrangement, an outer lumen 328 can be formed by an axial connection of a short section of a polyurethane tube in-between two sections of polyimide tube or in-between two sections of FEP tube, or in-between two sections of nylon tube. The polyurethane tube is positioned near the radial bend section of a steerable catheter. In another arrangement, a layer of tubing positioned coaxially over the outer diameter of the outer lumen 328 can be added to the arrangement above to stiffen particular sections of the outer lumen 328 to make it more rigid. The entire length of the outer lumen 328 encapsulates the two copper-nickel delivery tubes 332, which are positioned parallel to each other inside the outer lumen 328. The connections between the tubes 330, 332 are accomplished by a solder/braze material 334 (see FIG. 21). The hose 324 is also connected with the outer lumen 328 by a vacuum rated epoxy material, or by thermally bonding the two materials together, or using EV cured glue, to form an airtight seal 336. An inner handle piece 338 and an outer handle piece 340 are assembled over the various joints to protect the joints, and to provide a user-handling interface.

A strain relief 348 (see FIGS. 18, 19, 27, 40 and 47) is provided between the inner handle piece 338 and the outer lumen 328 at the distal end of the proximal section 304. The strain relief 348 is a flexible plastic or rubber tube, preferably made of nylon, polyurethane, polyethylene, or FEP, which functions to provide strain support to the catheter body 306 by distributing absorbed energy along its length.

The catheter body 306 includes two copper-nickel delivery tubes 332 positioned parallel within an outer lumen 328. The combination of material selections, physical sizes (as described below) and mechanical arrangement allows the catheter body 306 to be very flexible. The catheter body 306, along with the distal section 308 described below, is capable of bending around a contour having an angle of less than ninety degrees, having a bend radius of less than 0.50 inch.

The distal section 308 is a non-vacuum insulated section of the catheter 102, and contains the thermal transfer element (i.e., freezing element) defined by the single-loop 35C and non-insulated section of the delivery tube 332 as described below. The present invention provides several possible embodiments having the same distal section 308.

Smooth Tip Catheter

Figure 11:
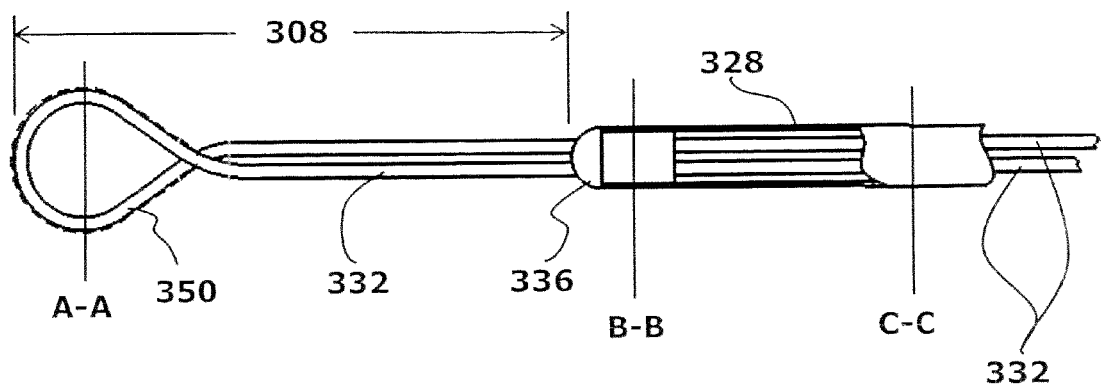
FIG. 11 is a cut-away side view of the distal section of one embodiment of the catheter of FIG. 10.
Figure 12:
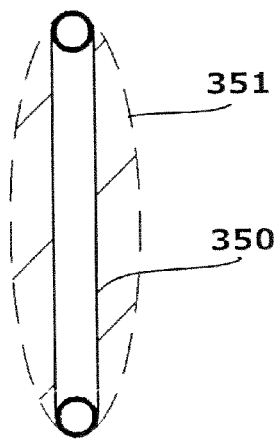
FIG. 12 is a cross-sectional view taken along line A-A in FIG. 11.
Figure 13:
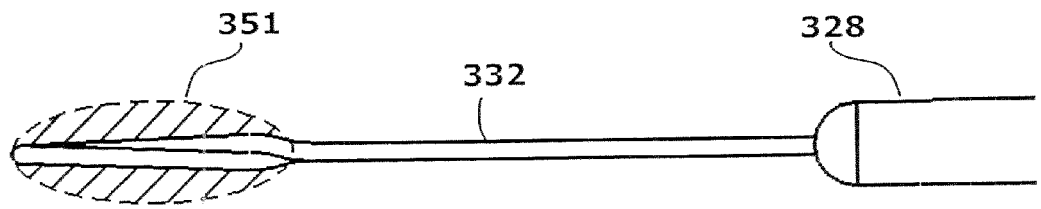
FIG. 13 is the same view as FIG. 11 but with the distal section rotated by ninety degrees.
Figure 14:
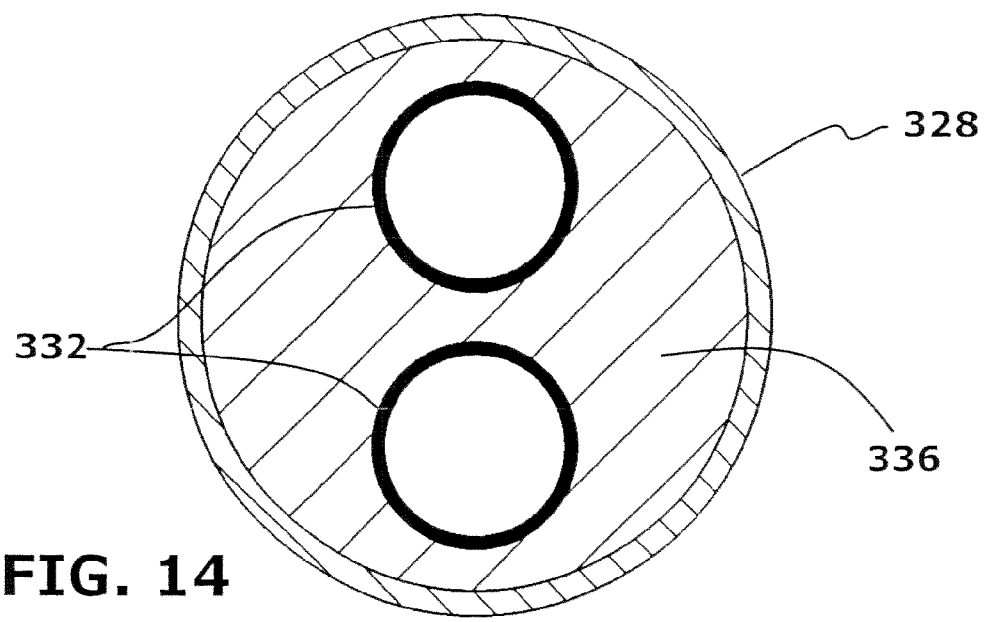
FIG. 14 is a cross-sectional view taken along line B-B in FIG. 11.
Figure 15:
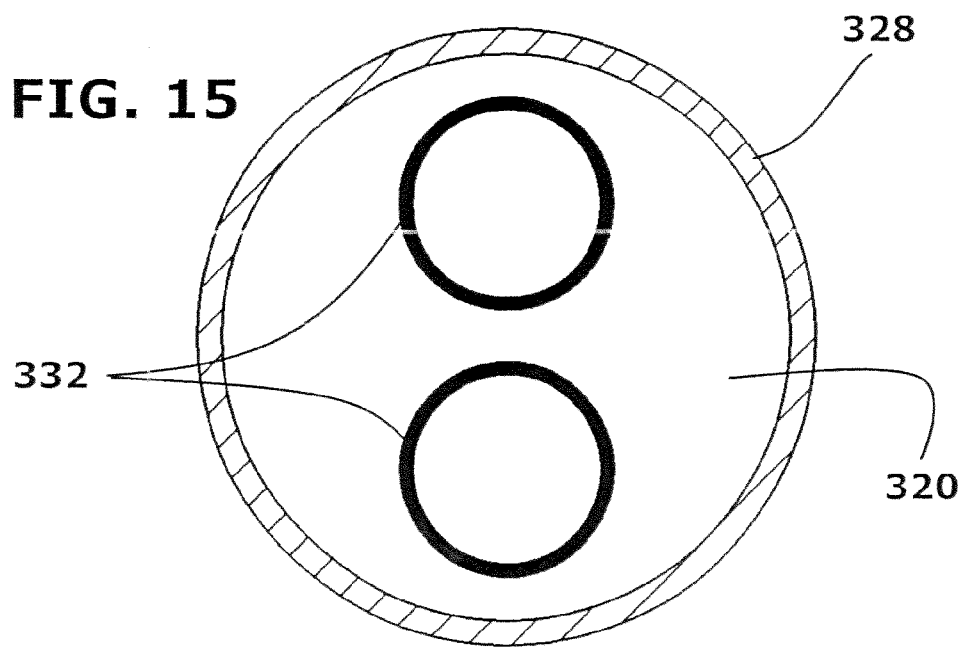
FIG. 15 is a cross-sectional view taken along line C-C in FIG. 11.

Referring to FIGS. 11-13, cryogen circulates from the connector section 300 to the distal section 308, and then back to the connector section 300 through a continuous pathway that forms a single-loop 350 at the distal section 308. The single pathway is defined by the tubes 330, 332, and with the single-loop 350 formed in the tube 332 that is located at the distal-most end of the distal section 308. The axis of the loop 350 is not concentric, but is perpendicular to the axis of the catheter's outer lumen 328. The delivery tube 332 is not insulated at the distal section 308 to facilitate maximum heat transfer capability.

This single-loop design is simple to manufacture and has fewer potential failure points. It minimizes the number of high-pressure connections. All the pressure joints are inside the catheter's outer lumen 328. Gas leakage within the catheter vacuum chamber 320 is captured. In addition, as described above, the system safety features monitor pressure level within the catheter vacuum chamber 320 and automatically purge unwanted gas away from the patient.

The single-loop 350 can be formed of a flexible material having good fatigue property. The material can made from annealed 70/30 Copper-Nickel alloy or stainless steel alloy with an outer diameter of 0.020 inches (0.508 mm) to 0.026 inches (0.660 mm) and an inner diameter of 0.016 inches (0.406 mm) to 0.020 inches (0.508 mm). The single-loop 350 element is designed to be able to slide through circular openings (i.e. the inlet port or opening of a conventional outer guiding catheter) having a diameter that is less than 0.105 inches (2.67 mm) or smaller than 8 French. The compactness as well as the flexibility of the single-loop 350 design enables it to enter the vascular structure easily. Adding filler material 351 (see FIGS. 12-13) to encapsulate the single-loop 350 makes the tip rounder and smoother, thereby resulting in near frictionless traction as the catheter 102 travels through the vascular structure. The filler element 351 can be made from a silver alloy or copper alloy by soldering/brazing, or using biocompatible epoxy.

The smooth tip catheter is the simplest, most cost-effective, compact, and flexible of all the configurations specified herein. This design has the least number of components and is the simplest to build. There is only one functional outer lumen 328 making the design small in diameter and flexible at the same time. This catheter is designed to be used in conjunction with a conventional outer guiding catheter.

Occluding Tip Catheter

FIGS. 25-28 illustrate another embodiment of a catheter that can be used with the present invention. FIGS. 25-28 illustrate an occluding tip catheter which has a smooth tip with the addition of a balloon 303 that is positioned proximal of the single-loop 350. The balloon 303 can be made from polyurethane film, nylon, or a PET material, and is positioned near the distal end of the catheter outer lumen 328 with one (distal) end of the balloon 303 formed with an airtight attachment to the catheter outer lumen 328. The second (proximal) end of the balloon 303 is formed with an airtight seal with a balloon delivery tube 305 that is made from a thin-walled and high-strength polyimide, nylon, PET, FEP, TEFLON™, or PEEK tubing. The balloon delivery tube 305 is covered and positioned concentrically about the catheter outer lumen 328, and carries balloon fluid 311 from a balloon connector port 309 of a balloon connector 307.

The balloon 303 functions to occlude the flow of blood and to center the distal end 308 within the blood vessel. Blood flow generates a constant heat source and, when directed over the freezing section, will reduce the cold energy being transferred to the treatment area. Heat energy from a high blood flow rate can reach an equilibrium point with the supplied cold energy at the distal end 308 and prevent further ice formation, thereby rendering the treatment ineffective. Therefore, occluding the blood flow allows cold energy to be delivered more effectively, and to concentrate the cold energy at the treatment area resulting in a more effective energy transfer approach.

The balloon 303 also serves to center the distal end 308 within the blood vessel. Centering of the distal end 308 allows uniform radial cold energy transfer resulting in a concentric treatment zone with the vessel wall. Without this feature, the treatment zone may not be concentric with the vessel wall, thereby possibly overtreating one side of the vessel while undertreating the opposite side. Thus, centering the distal end 308 within the vessel wall provides predictable outcomes and a controllable treatment procedure.

Prior to the freeze cycle, the balloon 303 is inflated to contact the vessel wall to occlude the blood vessel. During freeze treatment cycle, the blood surrounding the distal end 308 reaches freezing point and ice formation begins. Ice grows longitudinally and radially around the distal end 308, developing into an ice ball. Body heat is removed through the layer of frozen blood to the thermal transfer element/freezing element (i.e., the single-loop 350 and un-insulated section of the delivery tube 332) at the distal end 308. The catheter of this embodiment is designed to be used in conjunction with a conventional outer guiding catheter.

Balloon-Enclosed Tip Catheter

Figure 29:
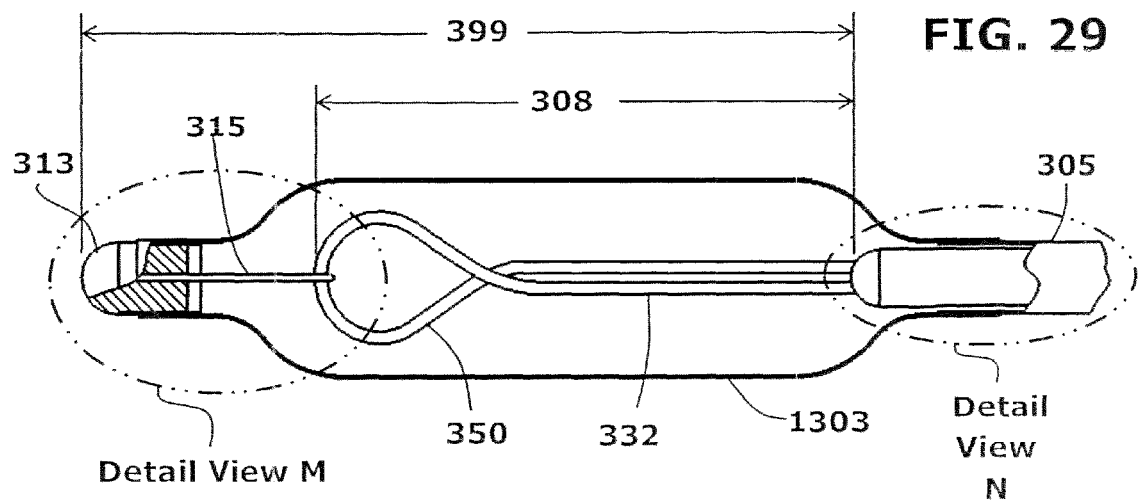
FIG. 29 is a cross-sectional side view of the distal section of another embodiment of the catheter of FIG. 10.
Figure 30:
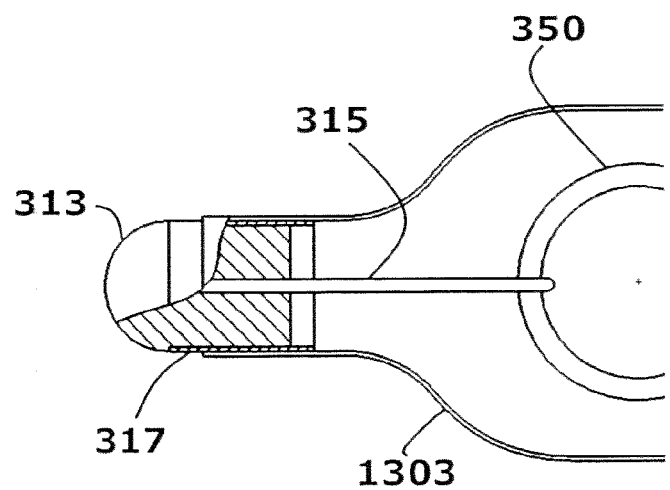
FIG. 30 is an enlarged cross-sectional side view of area M in FIG. 29.
Figure 31:
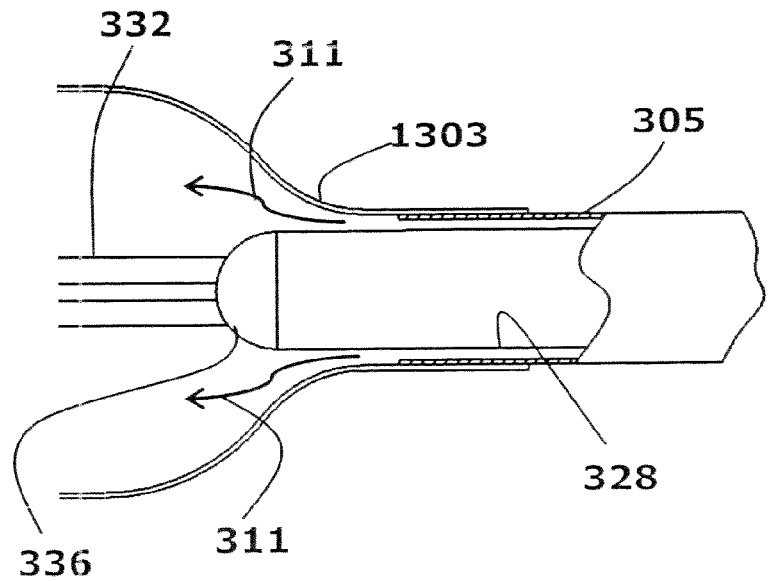
FIG. 31 is an enlarged cross-sectional side view of area N in FIG. 29.
Figure 32:
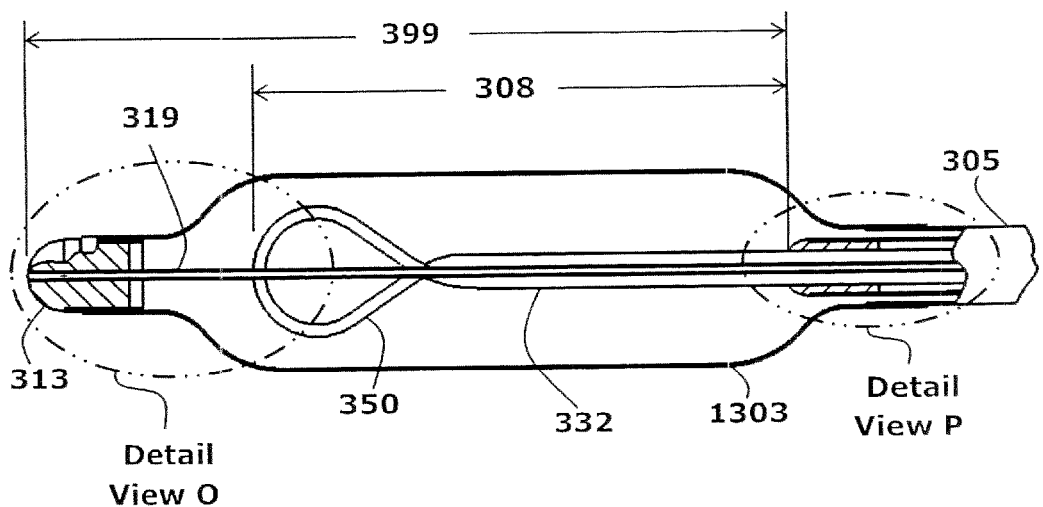
FIG. 32 is a cross-sectional side view of the distal section of another embodiment of the catheter of FIG. 10.
Figure 33:
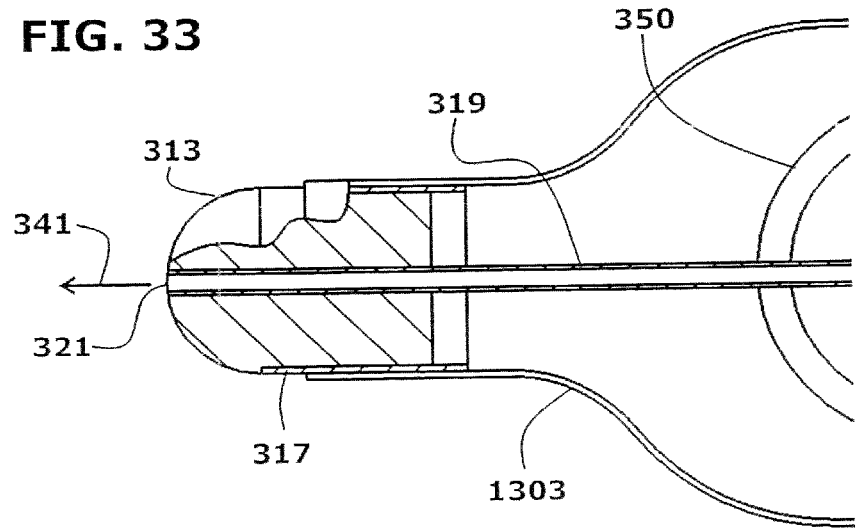
FIG. 33 is an enlarged cross-sectional side view of area O in FIG. 32.
Figure 34:
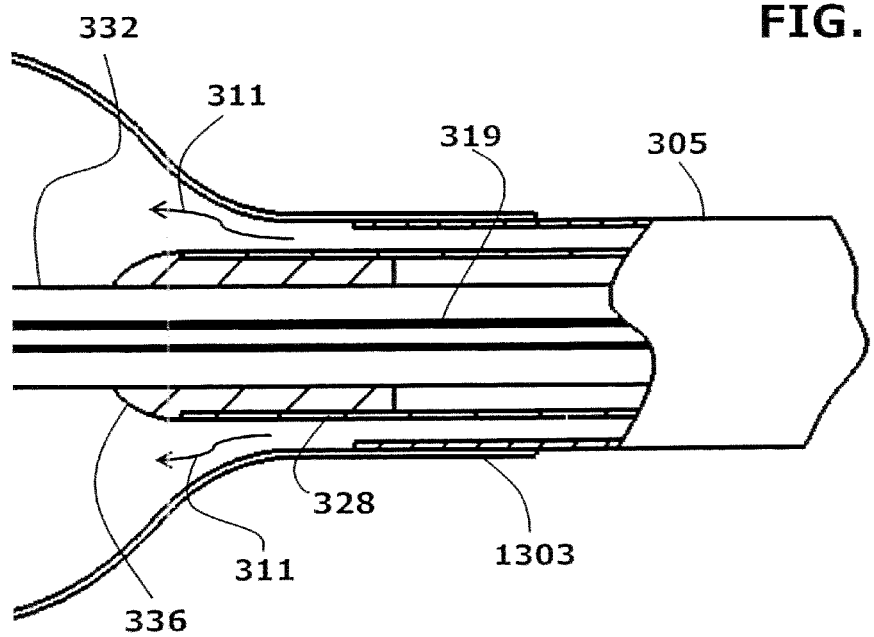
FIG. 34 is an enlarged cross-sectional side view of area P in FIG. 32.

FIGS. 29-31 illustrate another embodiment of a catheter that can be used with the present invention. FIGS. 29-31 illustrate a balloon-enclosed tip catheter, which has a "smooth tip catheter" encapsulated by a balloon similar in design to the balloon 303 described above. The balloon 1303 extends beyond both sides of the distal end 308, with one (proximal) side forming an airtight seal with a balloon delivery tube 305. The balloon delivery tube 305 carries balloon fluid 311 from a balloon connector port 309 of a three-way connector 307 that can be the same as that shown in FIG. 27. The other (distal) end of the balloon 1303 forms an airtight seal with the catheter tip outer tube 317 (see FIG. 30). The catheter tip outer tube 317 is made from the same material as balloon delivery tube 305. The internal cavity of the catheter tip outer tube 317 is filled with biocompatible epoxy forming a rounded outer epoxied tip 313 for ease of insertion through the vessel. A stainless steel spring wire 315 is embedded within the epoxied tip 313 on one end thereof, and soldered/brazed at the other end thereof to the single-loop 350 to simulate an extended distal end 399. The spring wire 315 has similar stiffness characteristics as the delivery tube 332 so as to enable the distal end 308 and spring wire 315 to be combined together forming an extended distal end 399 that mechanically behaves as a single unit. The spring wire 315 is also positioned at the epoxied tip 313 at a predetermined distance away from the tip of the single-loop 350, thereby preventing the insulated property of the epoxy from affecting ice formation and growth.

Figure 55:
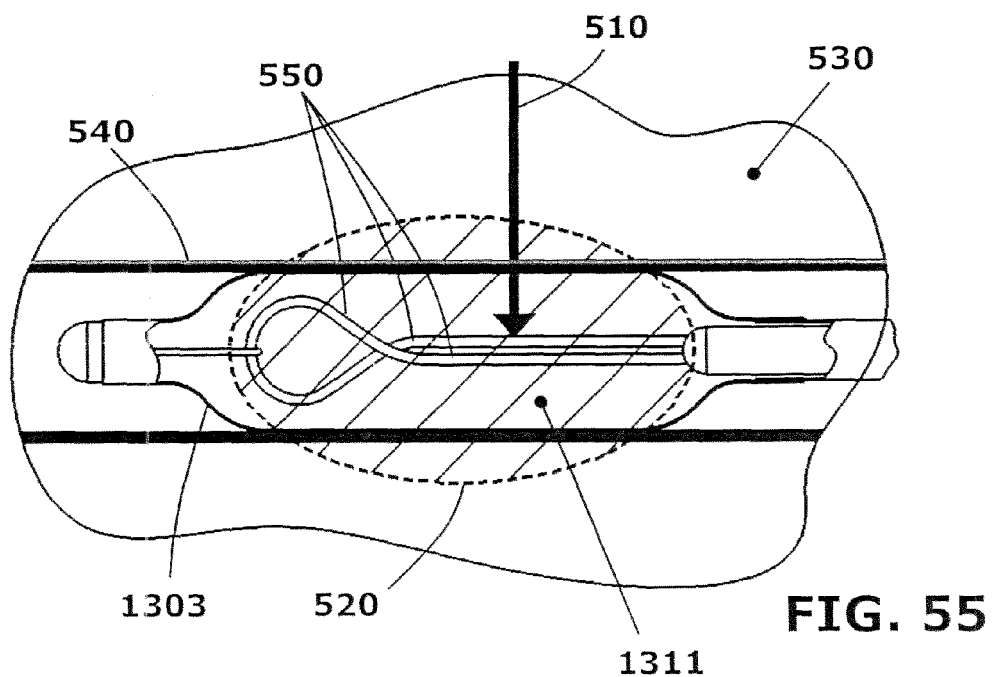
FIG. 55 illustrates the thermal transfer path during a freeze treatment cycle for the embodiment of FIG. 54.

The catheter of this embodiment is designed to be used in conjunction with a conventional outer guiding catheter. In normal operation, during a freeze cycle, the catheter 102 is positioned within a blood vessel, and then the balloon 1303 is inflated to contact the vessel wall. Once the balloon 1303 is inflated, the balloon wall contacts the blood vessel wall, thereby occluding blood flow through the artery. The volume of blood normally surrounding the distal end 308 is taken up by the volume of balloon fluid 311 that filled the inflated balloon 1303. The volume of balloon fluid 311 within the inflated balloon 1303 creates a thick layer of separation between the thermal transfer element/freezing element (i.e., the single-loop 350 and the un-insulated section of delivery tube 332) at the distal section 308 and the surrounding blood, thereby minimizing the freezing of blood. During the freeze treatment cycle, the fluid within the balloon 1303 changes into solid phase up to the balloon wall, and facilitates a direct conductive path with the vessel wall. Body heat is removed through the balloon wall and is conducted through the ice layer within the balloon 1303 to the thermal transfer element/freezing element 550 (i.e., the single-loop 350 and un-insulated section of delivery tube 332 as shown in FIG. 55) at the distal end 308. As the outer balloon wall drops below freezing point, ice formation begins and it grows through and beyond the vessel wall forming a mechanical/ice bond with the balloon outer wall. As shown in FIG. 55, thermal transfer path 510 draws heat from body tissue region 530 through the vessel wall 540 through the balloon 1303 and through the frozen balloon fluid 1311 to the thermal transfer element 550 to be carried away from the distal end 308 during a freeze treatment cycle. The ice that forms around the distal end 308 forms an ice ball outer boundary 520 that continuously increases to an equilibrium size with time.

Figure 56:
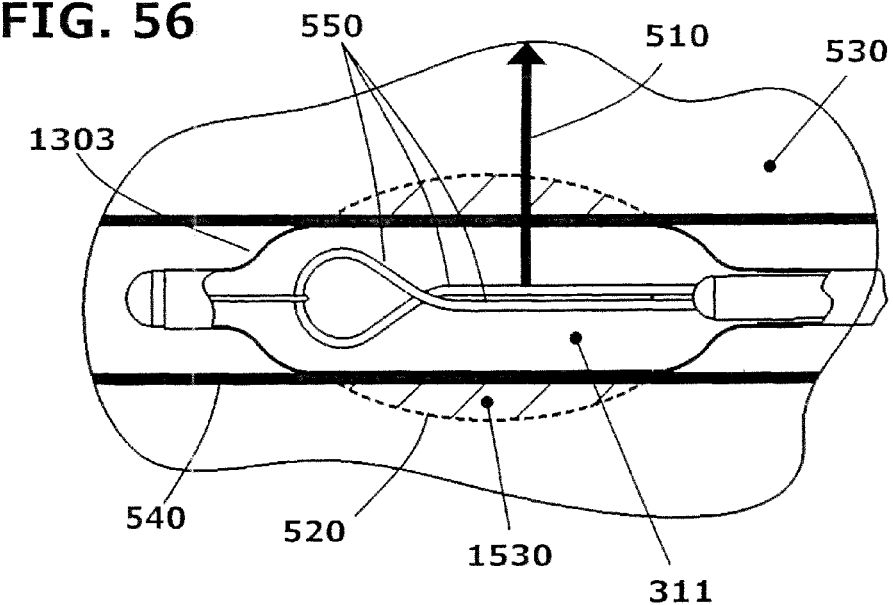
FIG. 56 illustrates the thermal transfer path during a thaw cycle for the embodiment of FIG. 54.

At the end of the freeze treatment cycle, a thaw cycle needed to melt the surrounding ice in preparation for catheter retrieval. During the thaw cycle, warm nitrogen gas feeds into the catheter gas connector 310 and begins conducting warm energy to the surrounding ice at the distal end 308 through the thermal transfer element 550. Ice surrounding the distal end 308 begins to melt and changes into liquid phase. The outer balloon wall acquires heat energy through the melted ice and its temperature begins to rise above freezing point, melting away the mechanical/ice bond that holds the outer balloon wall to the vessel wall. The catheter removal can be accomplished after extracting the fluid within the balloon 1303. As shown in FIG. 56, heat energy radiates from the thermal transfer element 550 and thaw the surrounding ice into balloon fluid 311. Heat energy further travels through the balloon wall 1303, the vessel wall 540, and to the body tissue 530 to melt the surrounding ice. The catheter 102 can be removed even though body tissue region 1530 is not yet thawed. The temperature of surrounding tissue further increases with up to the maximum temperature of the delivered warm nitrogen gas.

FIGS. 58-61 illustrate other embodiments of balloon-enclosed tip catheters:

A. Flexible Soft Tip Catheter

Figure 58:
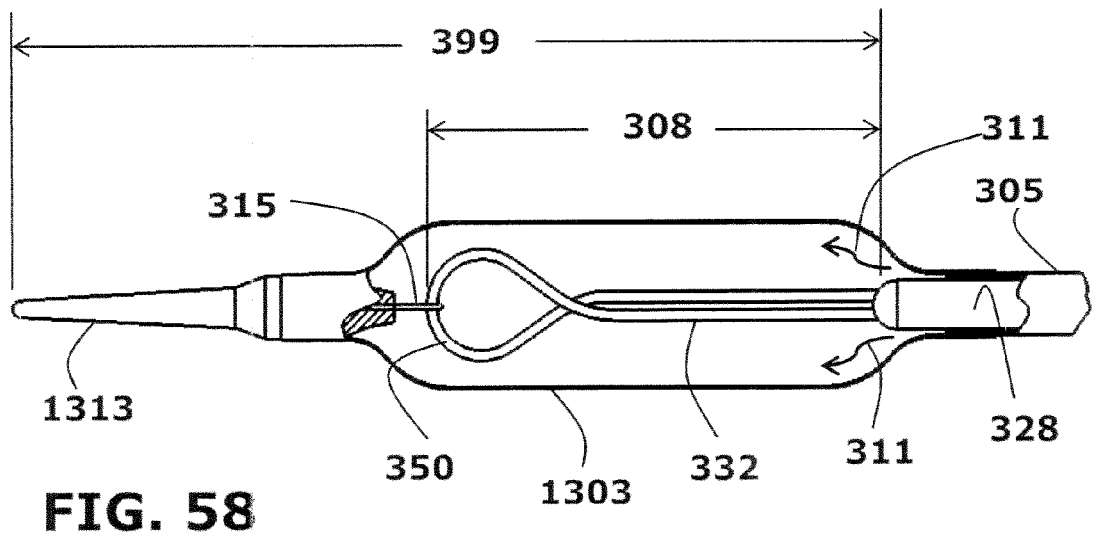
FIG. 58 is a cross-sectional side view of the distal section of yet another embodiment of the catheter of FIG. 10.

FIG. 58 illustrates one variation of a balloon-enclosed tip catheter embodiment that can be used with the present invention. FIG. 58 illustrates a balloon-enclosed tip catheter which has a smooth tip encapsulated by a balloon similar in design to the balloon 1303 described above. The balloon 1303 extends beyond both sides of the distal end 308, with one (proximal) side forming an airtight seal with a balloon delivery tube 305. The balloon delivery tube 305 carries balloon fluid 311 from a balloon connector port 309 of a three-way connector 307 that can be the same as that shown in FIG. 27. The other (distal) end of the balloon 1303 forms an airtight seal with a flexible soft tip 1313. The flexible soft tip 1313 is made from a biocompatible soft material (such as Pebax 2533 with 50% BaSO$_4$) that also has a radiopaque characteristic. The radiopaque feature provides a visual feedback as to the location of the catheter tip, thereby enabling proper catheter placement within the treatment region.

A stainless steel spring wire 315 is embedded within the flexible soft tip 1313, forming an airtight seal on one end thereof, and soldered/brazed at the other end thereof to the single-loop 350 to simulate an extended distal end 399. The spring wire 315 has similar stiffness characteristics as the delivery tube 332 so as to enable the distal end 308 and spring wire 315 to be combined together forming an extended distal end 399 that mechanically behaves as a single unit. The spring wire 315 is also positioned at the catheter soft tip 1313 at a predetermined distance away from the tip of the single-loop 350, thereby preventing the insulated property of the catheter soft tip material from affecting ice formation and growth.

The flexible soft tip 1313 of the present embodiment replaces the outer epoxied tip 313 and the catheter tip outer tube 317 of the balloon-enclosed tip catheter embodiment described above in FIGS. 29-31. This modification provides improved maneuverability during catheter introduction into the vascular structure, enabling the tip 1313 to flex and lead the catheter around torturous passages. The flexible soft tip 1313 is an improvement over the hardened outer epoxied tip 313 by alleviating damage caused to the inner vessel walls during catheter insertion and removal.

B. Embedded Single-Loop Catheter

Figure 59:
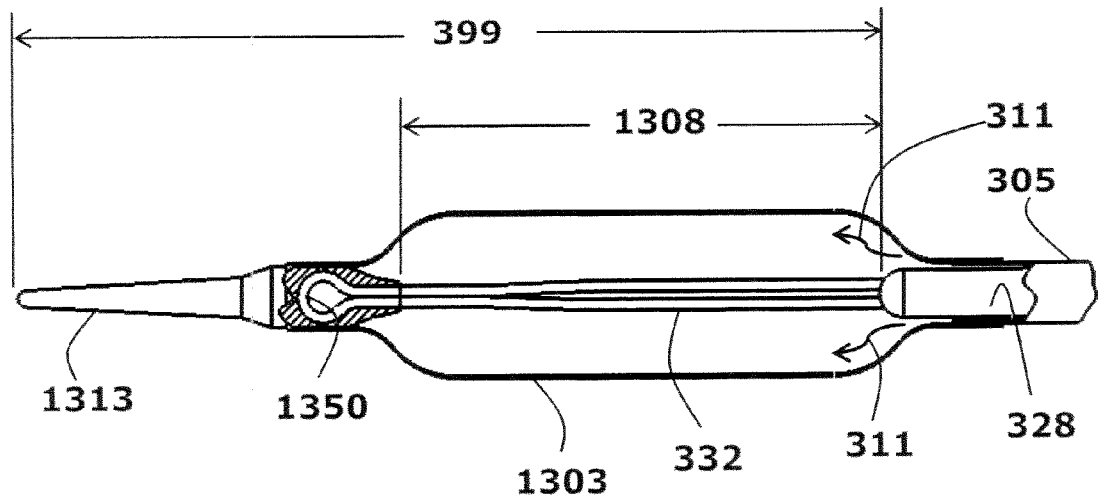
FIG. 59 is a cross-sectional side view of the distal section of a further embodiment of the catheter of FIG. 10.

FIG. 59 illustrates modifications to the principles illustrated in the embodiment of FIG. 58. FIG. 59 illustrates a balloon-enclosed tip catheter having a single-loop element 1350 embedded within the flexible soft tip 1313 forming an airtight seal between the two components. The balloon 1303 extends beyond both sides of the distal end 308, with one (proximal) side forming an airtight seal with a balloon delivery tube 305. The balloon delivery tube 305 carries balloon fluid 311 from a balloon connector port 309 of a three-way connector 307 that can be the same as that shown in FIG. 27. The other (distal) end of the balloon 1303 forms an airtight seal with the flexible soft tip 1313.

Elimination of the stainless steel spring wire 315 from the embedded single-loop element embodiment of FIG. 58 requires a longer distal section 308 that extends and connects to the flexible soft tip 1313. This extended distal section 1308 provides addition thermal transfer surface areas within the ablation section, thereby enhancing the thermal transfer rate, which varies linearly with changes in surface area.

C. Embedded Single-Loop with Single Coil Catheter

Figure 60:
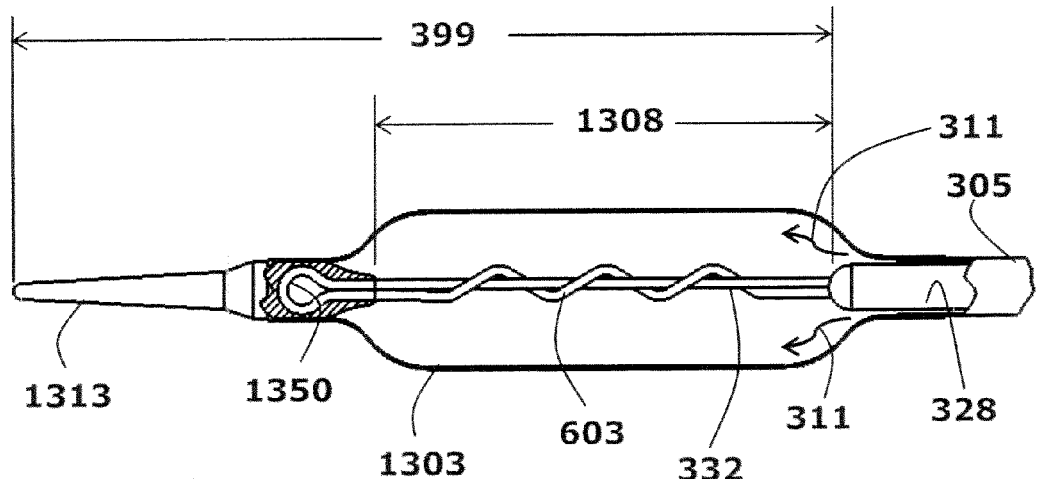
FIG. 60 is a cross-sectional side view of the distal section of another embodiment of the catheter of FIG. 10.

FIG. 60 illustrates modifications to the principles illustrated in the embodiments of FIGS. 58-59. FIG. 60 illustrates a balloon-enclosed tip catheter which contains a single coil 603 incorporated in series with a single-loop element 1350 that defines the ablation section or distal end 1308. The single coil 603 is formed by coiling one of the two delivery tubes 332 about the outer diameter of the second tube. Otherwise, the embodiment of FIG. 60 has the same construction as the embodiment of FIG. 59.

The extended distal section 1308 allows for additional performance improvement features. For example, integrating a single coil 603 within the extended distal end 1308 provides further enhancement in performance to the embedded single-loop element catheter design due to an increase in thermal transfer surface areas. The single coil 603 extends radially at portions thereof when compared to a straight tube, thereby effectively harnessing thermal energy at larger diameters, resulting in larger radial ablation.

D. Embedded Single-Loop with Double Coil Catheter

Figure 61:
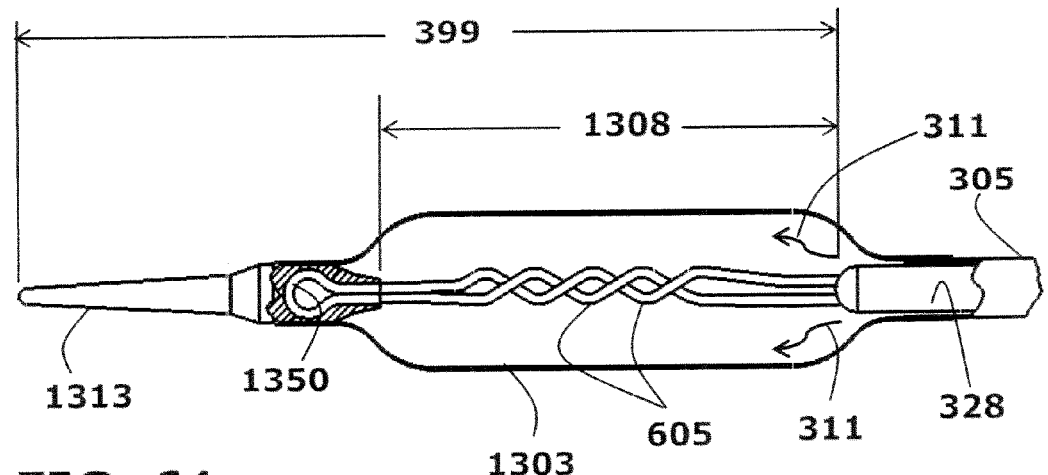
FIG. 61 is a cross-sectional side view of the distal section of yet another embodiment of the catheter of FIG. 10.

FIG. 61 illustrates a modifications to the principles illustrated in the embodiments of FIGS. 58-60. FIG. 61 illustrates a balloon-enclosed tip catheter having a double coil 605 incorporated in series with a single-loop element 1350 that define the ablation section or extended distal end 1308. The double coil 605 is formed by coiling two delivery tubes 332 concentrically about the centerline of the outer lumen 328. The single-loop element 1350 is embedded within the flexible soft tip 1313 forming an airtight seal between the two components. Otherwise, the embodiment of FIG. 61 has the same construction as the embodiment of FIG. 60.

Integrating a double coil 605 within the distal end 1308 provides further performance enhancement to the embedded single-loop with single coil catheter design due to an increase in thermal transfer surface. The double coil 605 extends radially at portions thereof when compared to a straight tube, thereby effectively harnessing thermal energy at larger diameters. This embodiment may be the most effective of these balloon-enclosed tip catheter embodiments for treating a larger radial ablation zone.

Steerable Catheter with Angiogram Tube Positioned within Vacuum Chamber

Figure 40:
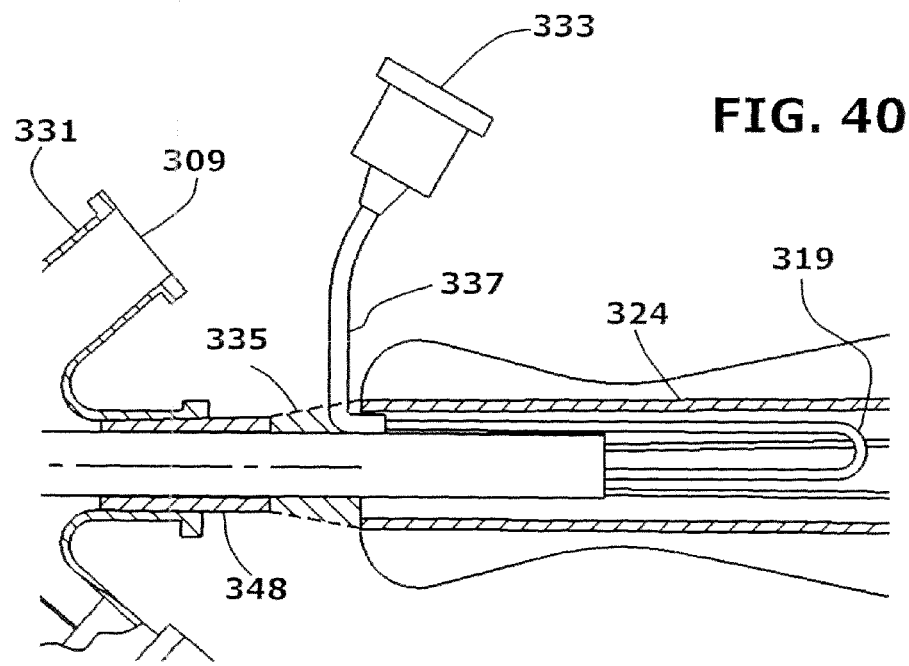
FIG. 40 is a cross-sectional side view of the area S in FIG. 38.
Figure 41:
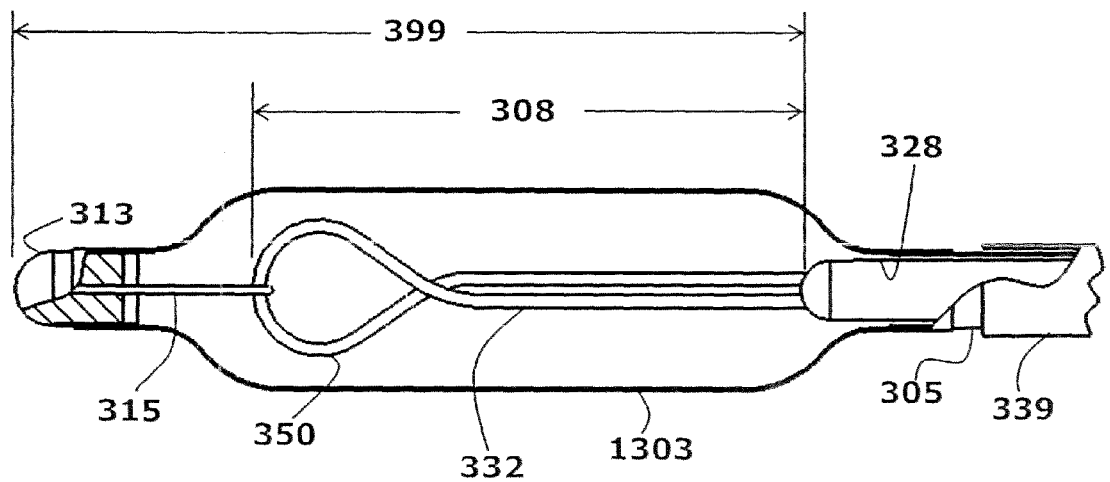
FIG. 41 is a cut-away side view of the distal section of yet another embodiment of the catheter of FIG. 10.
Figure 42:
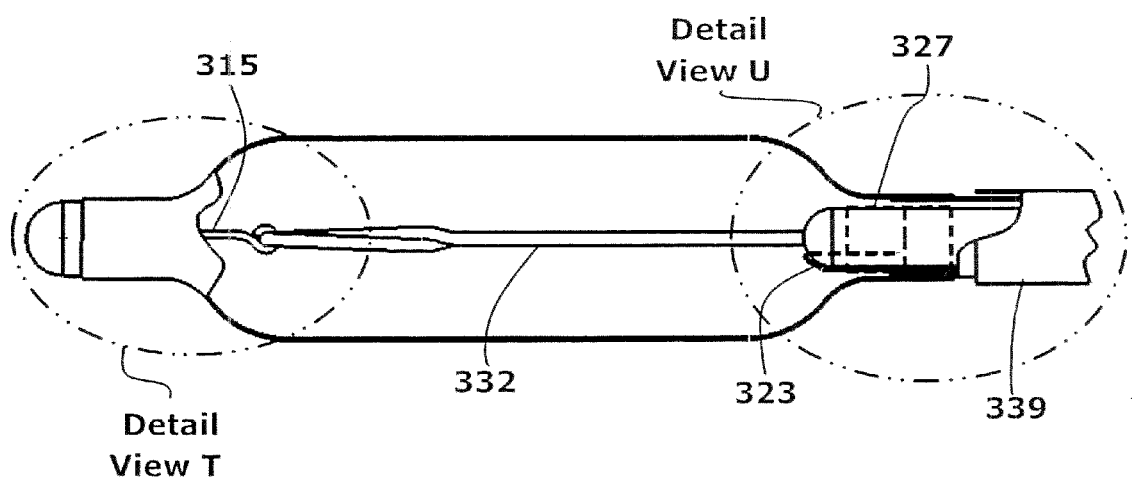
FIG. 42 is a cross-sectional side view of FIG. 41 but with the distal section rotated by ninety degrees.
Figure 43:
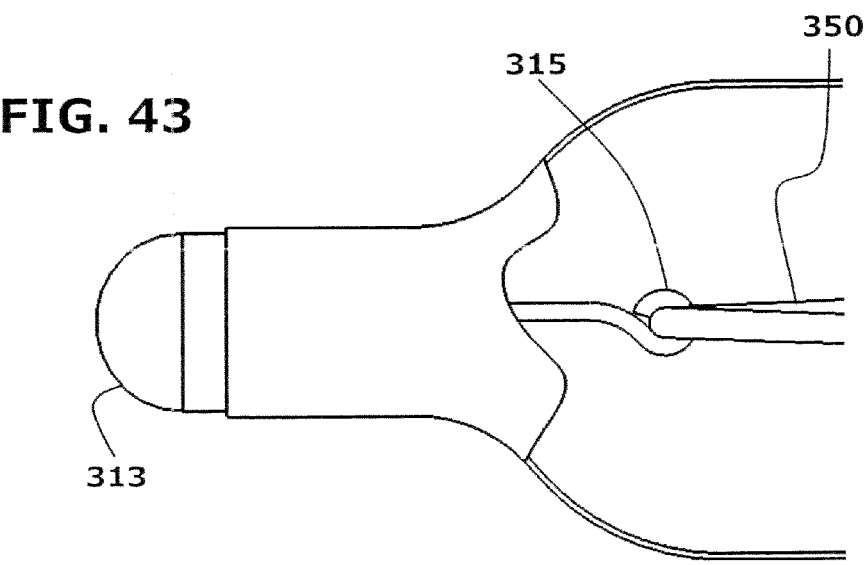
FIG. 43 is an enlarged cut-away side view of area T in FIG. 42.

FIGS. 32-40 illustrate another embodiment according to the present invention, which is a steerable catheter with an angiogram tube positioned within the vacuum chamber. This embodiment is a variation of the embodiment in FIGS. 29-31, but with the spring wire 315 replaced by an annealed stainless steel angiogram tube 319, and further including the addition of a pull wire 323 for steering capability. The distal end of the angiogram tube 319 is embedded within the epoxied tip 313, and carries an angiogram outlet port 321 positioned at its distal tip end. The angiogram tube 319 connects the epoxied tip 313 and the seal 336, and extends parallel along the delivery tube 332 and is captured within the catheter outer lumen 328. A portion of the angiogram tube 319 is placed within the catheter vacuum chamber 320 captured in between two airtight seals 336 and 335. As shown in FIG. 40, the angiogram tube 319 exits the seal 335 and is connected to a flexible angiogram tube 337 to receive angiogram fluid 341 from an angiogram inlet port 333.

Figure 35:
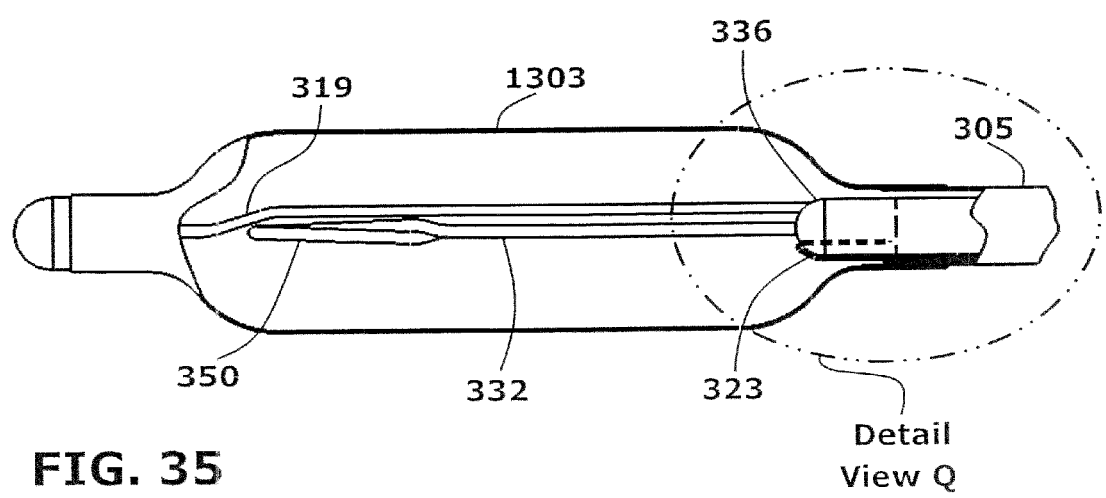
FIG. 35 is a partial exterior cut-away side view of FIG. 32 but with the distal section rotated by ninety degrees.
Figure 36:
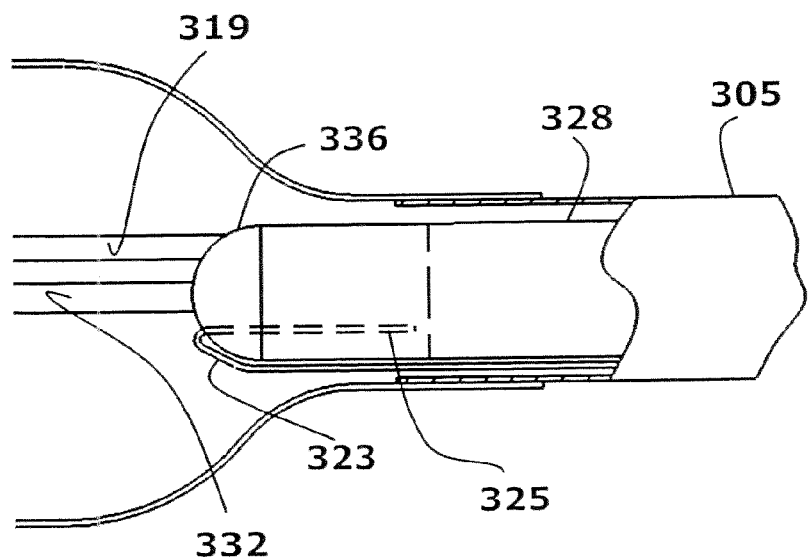
FIG. 36 is an enlarged cut-away side view of the area Q in FIG. 35.
Figure 37:
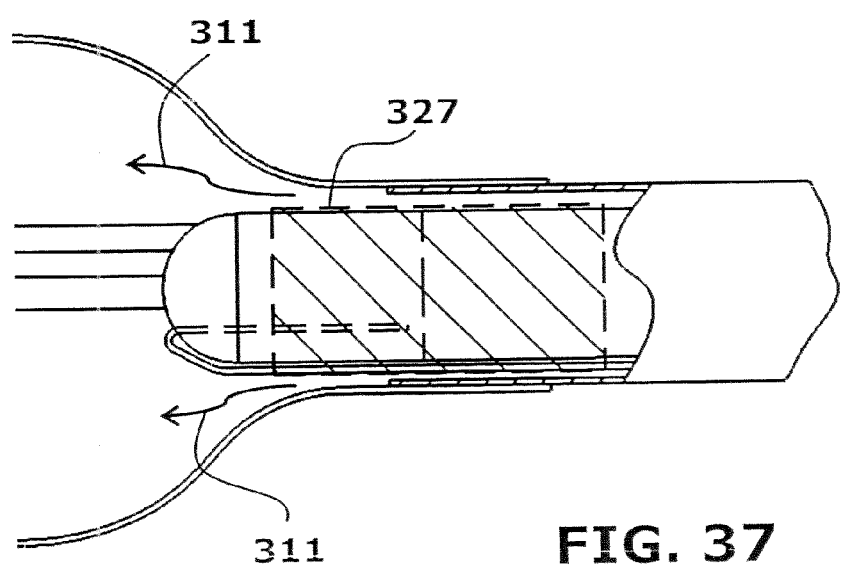
FIG. 37 is the same view as FIG. 36 but with the addition of the heat shrink tube.
Figure 38:
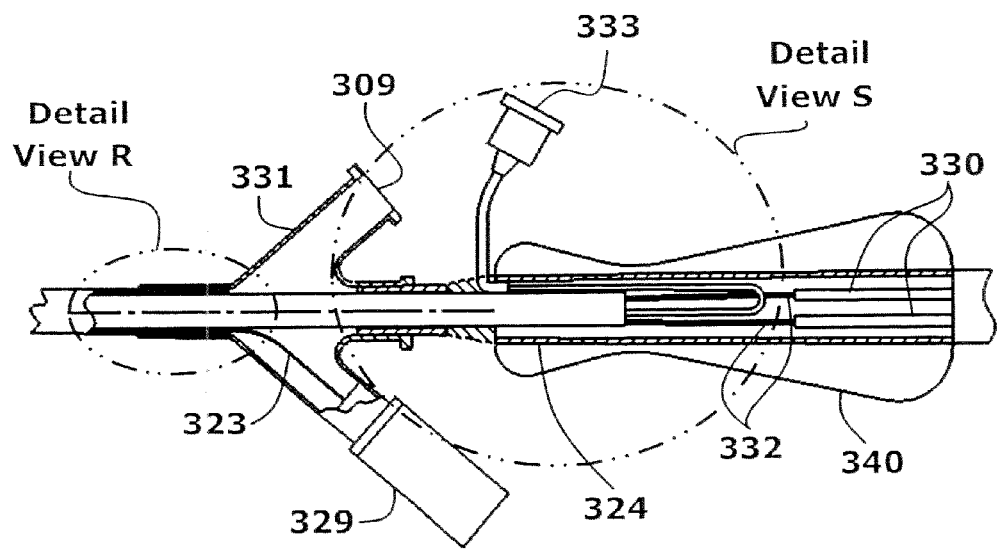
FIG. 38 is a cross-sectional side view of the proximal portion of the catheter of FIG. 32.
Figure 39:
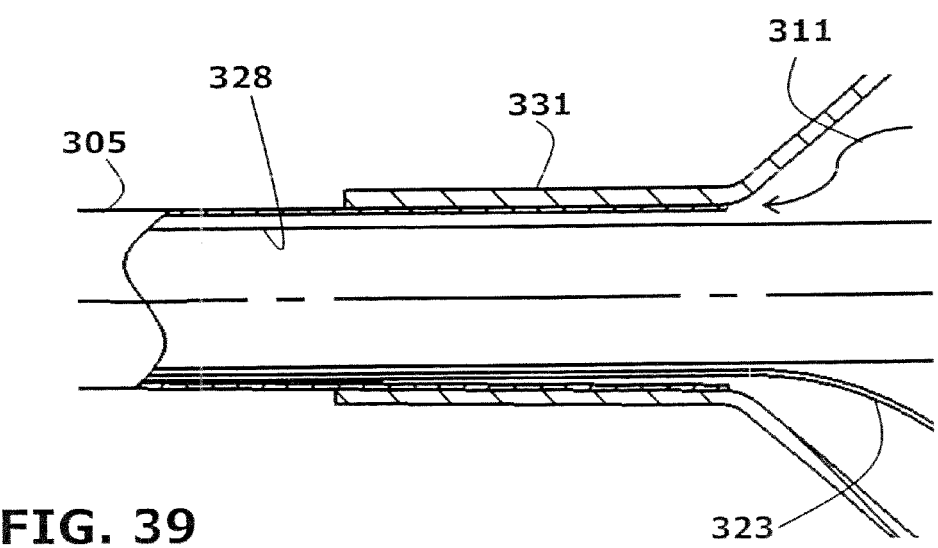
FIG. 39 is a cross-sectional side view of the area R in FIG. 38.

The steerable catheter incorporates a stainless steel pull wire 323 for steering as depicted in FIGS. 35-37. One end 325 of the pull wire 323 is permanently embedded within the airtight seal 336 serving as an anchor point. The pull wire 323 then makes a 180-degree turn as it exits the seal 336, extends between the balloon delivery tube 305 and the catheter outer lumen 328, and then terminates at the steerable adjuster 329 that is mounted to the four-way connector 331 (see FIG. 38). As shown in FIG. 37, a holding tube 327 holds the pull wire 323 to the catheter outer lumen 328, forming a tight radial clamp that holds both components together but still allows relative axial movement between the pull wire 323 and the catheter outer lumen 328. When tension is applied to the pull wire 323 through the steerable adjuster 329, the overall length of the pull wire 323 shortened. The catheter outer tube 328 is forced to comply with the shortened length of the pull wire 323 by making a radial bend. The catheter outer tube 328 bends radially on the side that is in contact with the pull wire 323, with its inner bend radius having a shorter circumferential length to comply with the shortened pull wire length. The holding tube 327 is positioned along the length of radial bend section of the outer lumen 328. Without the holding tube 327 holding the outer lumen 328 and the pull wire 323 together, both components may separate as tension is applied to the pull wire 323. The outer lumen 328 will bend but the pull wire 323 will remain straight due to the pulling force. The two parts separate at the bend section and could tear and rip the blood vessel apart.

Having an angiogram outlet port 321 positioned at the distal tip of the catheter ensures that angiogram fluid 341 will flow to the designated treatment area without obstructions. However, the additional angiogram tube 319 will make the overall design stiffer, and the catheter outer lumen 328 larger, in order to accommodate the angiogram tube 319. The catheter configuration of this embodiment is the stiffest of all embodiments herein. Although the overall catheter outer profile of this embodiment is larger and stiffer, this embodiment provides a complete package and can work independently without needing any additional guiding catheter or accessories as may be required by the embodiments disclosed above. When the above embodiments include a guiding catheter, they will have a larger overall profile.

Steerable Catheter with Angiogram Tube Placed Outside the Vacuum Chamber

Figure 44:
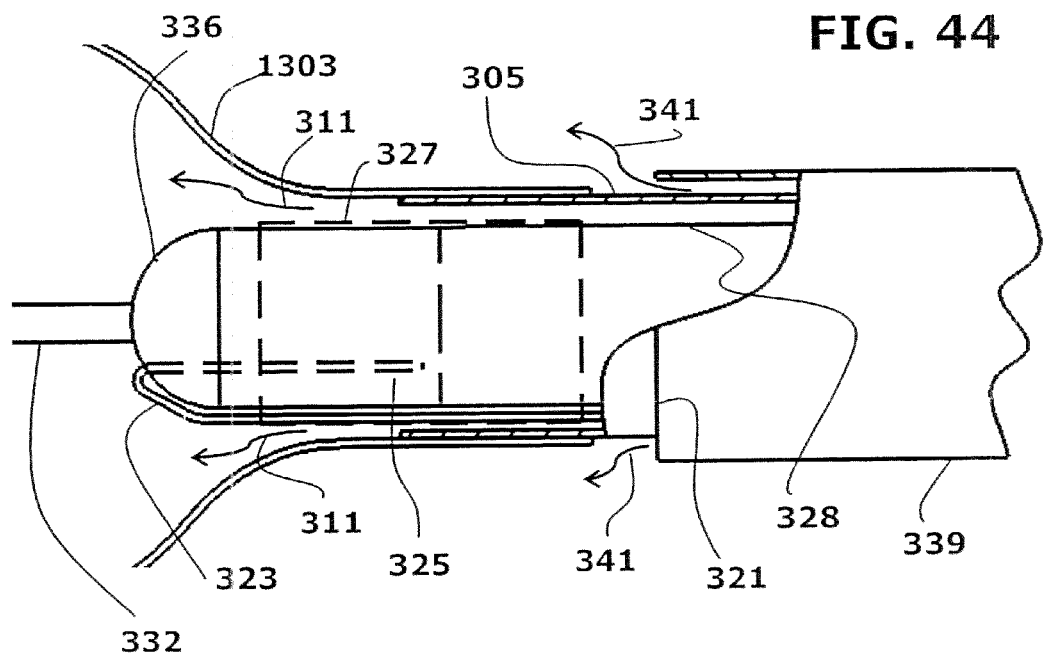
FIG. 44 is an enlarged cross-sectional side view of area U in FIG. 42.
Figure 45:
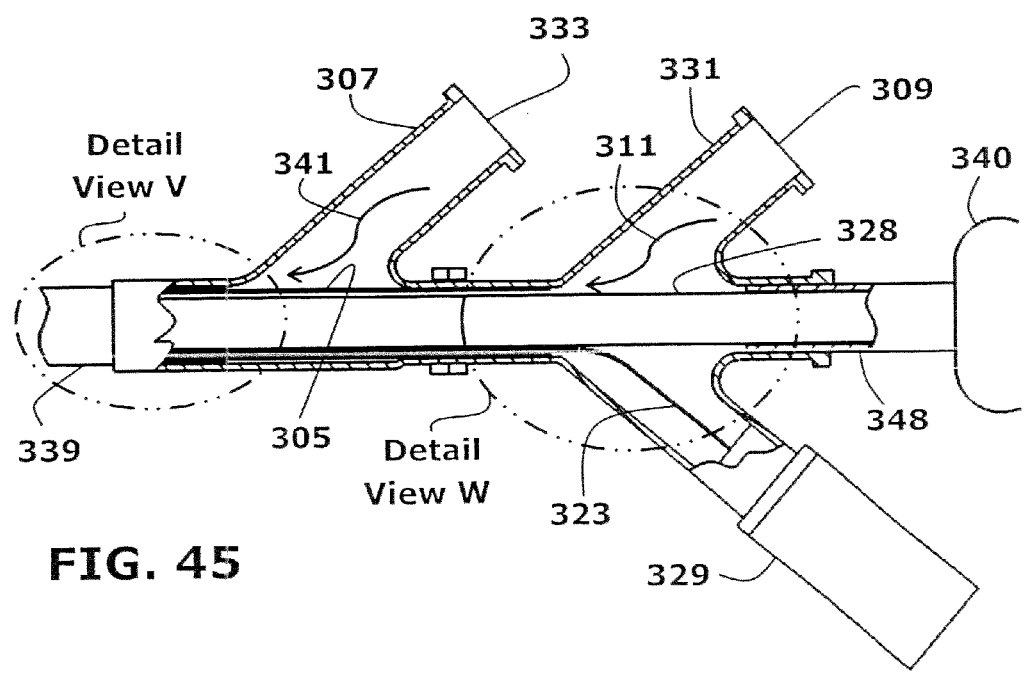
FIG. 45 is a cross-sectional side view of the proximal portion of the catheter of FIG. 41.
Figure 46:
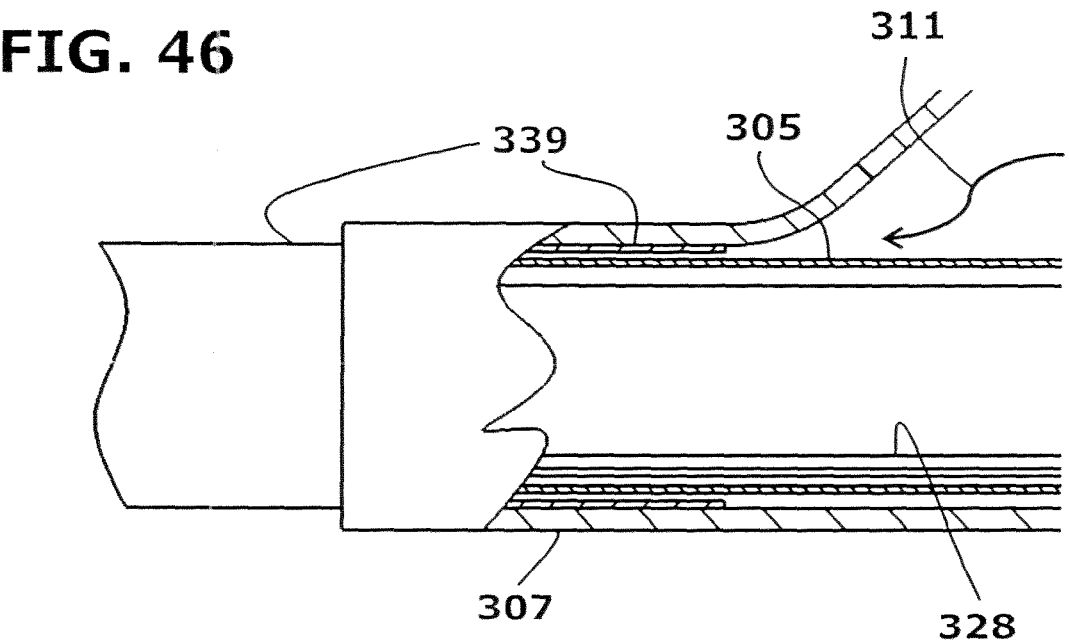
FIG. 46 is a cross-sectional side view of the area V in FIG. 45.
Figure 47:
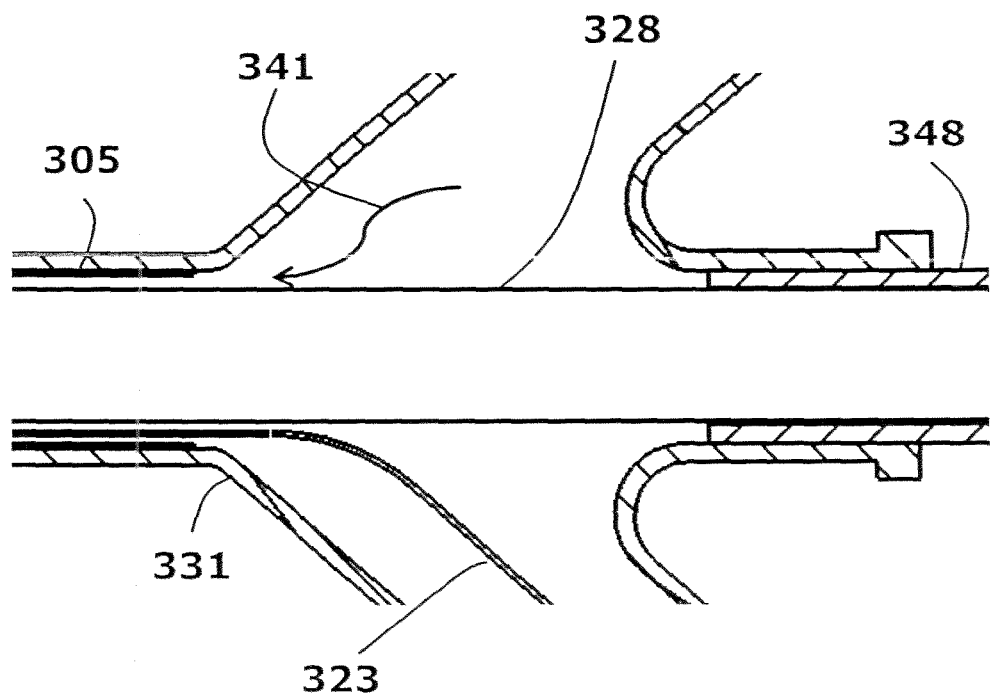
FIG. 47 is a cross-sectional side view of the area W in FIG. 45.
Figure 48:
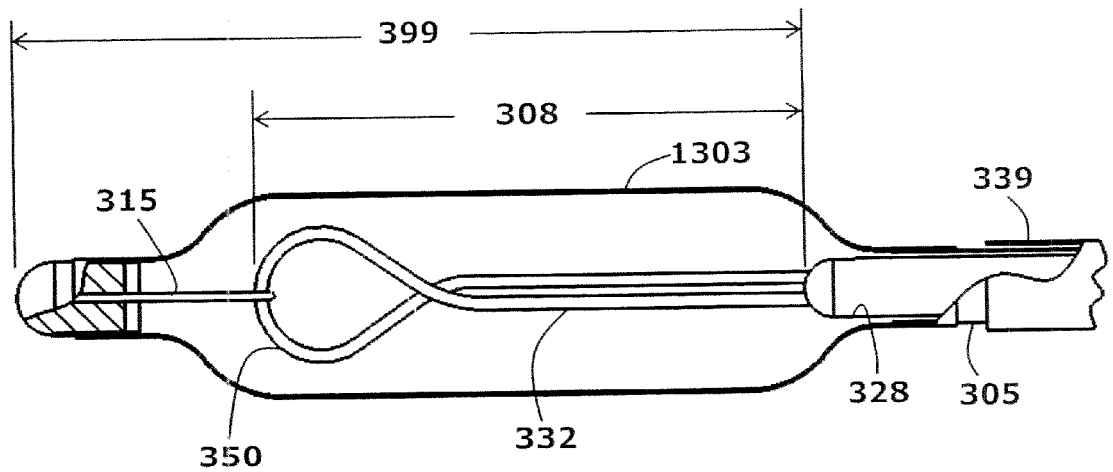
FIG. 48 is a cut-away side view of the distal section of yet another embodiment of the catheter of FIG. 10.
Figure 49:
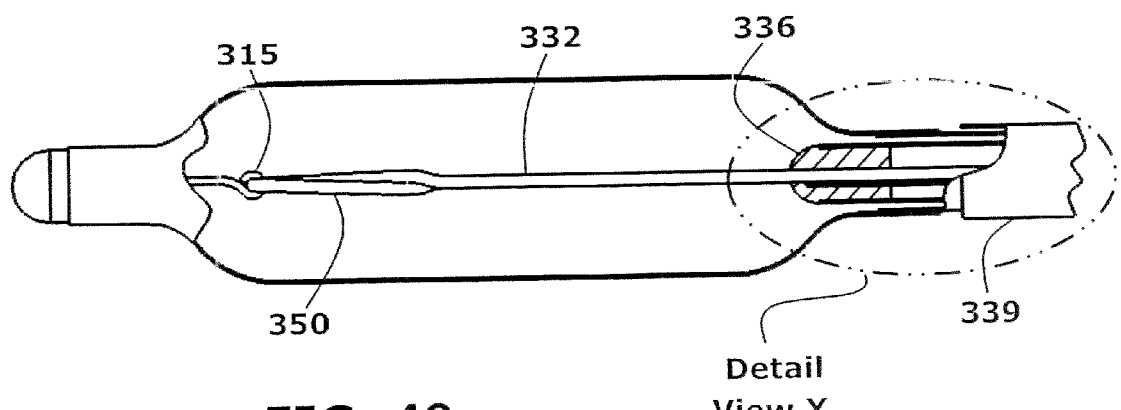
FIG. 49 is a side view of FIG. 48 with the distal section rotated by ninety degrees.
Figure 50:
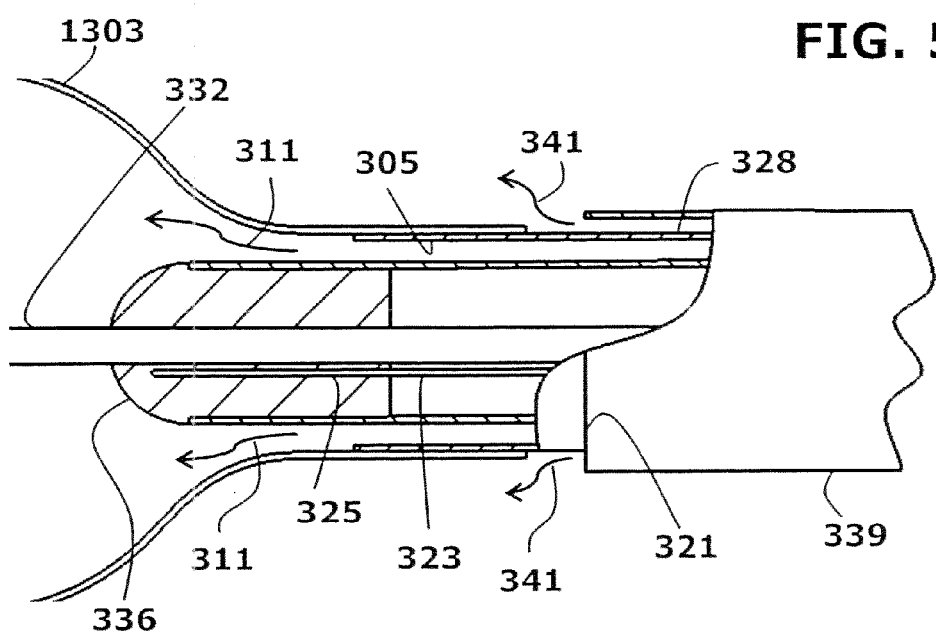
FIG. 50 is an enlarged cut-away side view of area X in FIG. 49.

FIGS. 41-47 illustrate another embodiment of the present invention, which is a steerable catheter having an angiogram tube placed outside the vacuum chamber. This embodiment is a variation of the embodiment in FIGS. 29-31 (with the spring wire 315), but with the addition of a pull wire 323 for steering capability and an outer angiogram delivery lumen 339. The pull wire 323 has the same construction as the pull wire 323 in FIGS. 32-40 above. One end 325 of the pull wire 323 is permanently embedded within an airtight seal 336 serving as an anchor point. The pull wire 323 makes a 180-degree turn as it exits the seal 336, extends in between the balloon delivery tube 305 and the catheter outer lumen 328, and then terminates at the steerable adjuster 329 mounted to the four-way connector 331 (see FIG. 45). As shown in FIG. 44, a holding tube 327 holds the pull wire 323 to the catheter outer lumen 328, forming a tight radial clamp that holds both components together but still allowing relative axial movement between the pull wire 323 and the catheter outer lumen 328. When tension is applied to the pull wire 323 through the steerable adjuster 329, the overall length of the pull wire 323 is shortened. The catheter outer tube 328 forced to comply with the shortened length of the pull wire 323 by making a radial bend. The catheter outer tube 328 bends radially on the side that is in contact with the pull wire 323, with its inner bend radius having shorter circumferential length to comply with. The shortened pull wire length. The holding tube 327 is positioned along the length of radial bend section of the outer lumen 328. Without the holding tube 327 holding the outer lumen 328 and the pull wire 323 together, both components may separate as tension applied to the pull wire 323. The outer lumen 328 will bend but the pull wire 323 will remain straight due to the pulling force. The two parts may separate at the bend section and could tear and rip blood vessel apart.

As best shown in FIGS. 44-47, the outer angiogram delivery lumen 339 is positioned concentrically outside the balloon delivery tube 305, and receives angiogram fluid 341 from the angiogram inlet port 333 of the three-way connector 307 that is in proximity to the handle 340. The distal end of the outer angiogram delivery lumen 339 defines the angiogram outlet port 321 (see FIG. 44), which is the circumferential area or opening between the balloon delivery tube 305 and the outer angiogram delivery lumen 339.

This embodiment has a smaller outer profile and is more flexible than the embodiment of FIGS. 32-40. Positioning the angiogram outlet port 321 more proximally from the distal end 308 is preferred as the user can see the entire distal end 308 of the catheter, as well as the state of blood vessel occlusion during treatment. This construction of this embodiment is a complete package, and can be used independently without needing additional guiding catheters or accessories, as may be required by the embodiments disclosed above.

Steerable Catheter with Pull Wire Placed within the Vacuum Chamber

FIGS. 48-54 illustrate yet another embodiment of the present invention, which is a steerable catheter having a pull wire placed within the vacuum chamber. This embodiment is a variation of the embodiment in FIGS. 29-31 (with the spring wire 315), but with the addition of an outer angiogram delivery lumen 339 and a pull wire 323 for steering capability. The outer angiogram delivery lumen 339 has the same construction as that which is described in FIGS. 41-47, and is positioned concentrically outside the balloon delivery tube 305 and receives angiogram fluid 341 from the angiogram inlet port 333 of the three-way connector 307 that is in proximity to the handle 340. The distal end of the outer angiogram delivery lumen 339 defines the angiogram outlet port 321 (see FIG. 50), which is the circumferential area or opening between the balloon delivery tube 305 and the outer angiogram delivery lumen 339.

Figure 51:
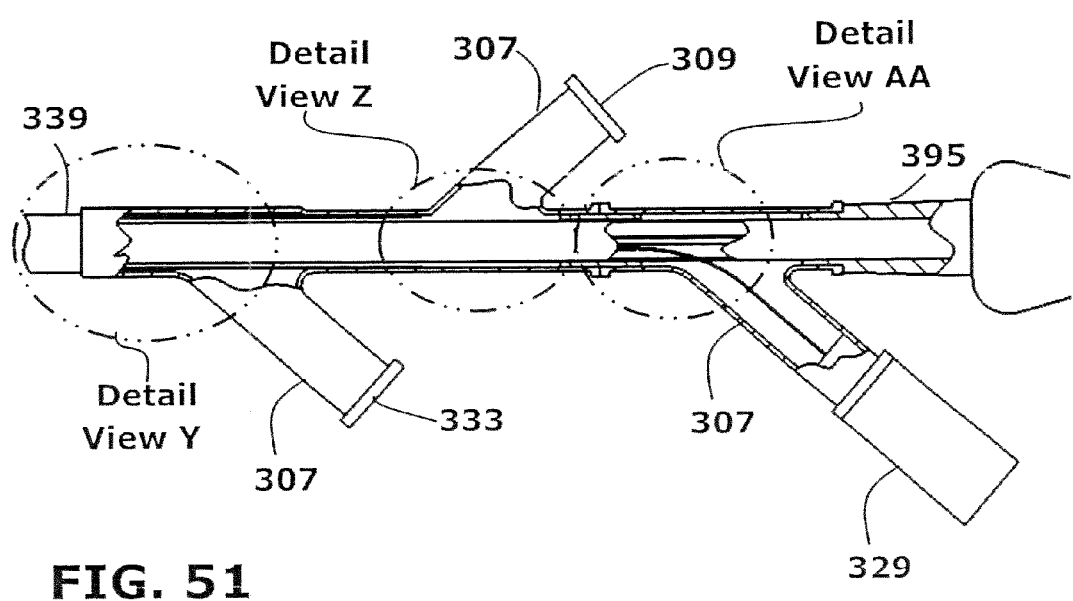
FIG. 51 is a cross-sectional side view of the proximal portion of the catheter of FIG. 48.
Figure 52:
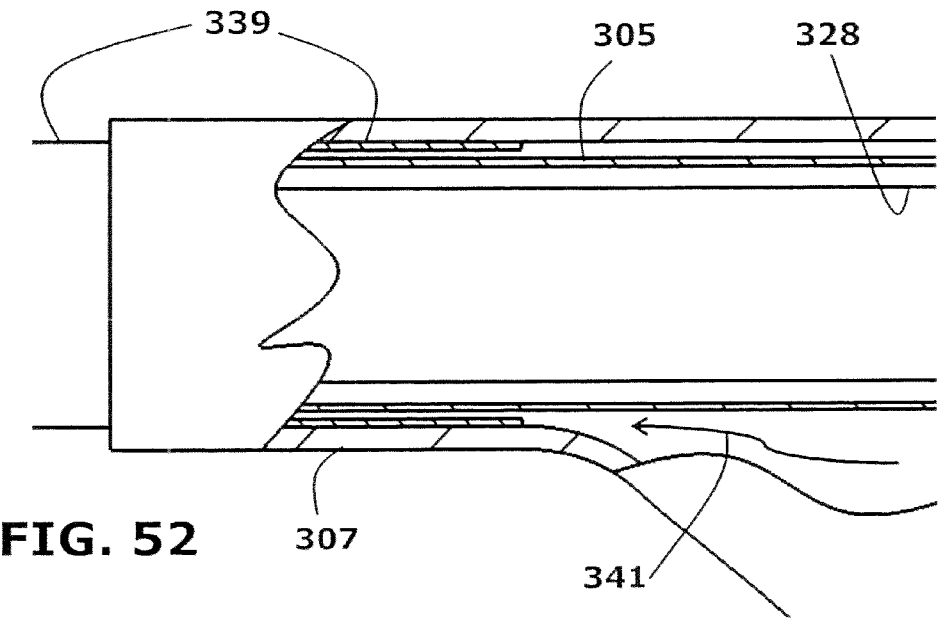
FIG. 52 is a cross-sectional side view of the area Y in FIG. 51.
Figure 53:
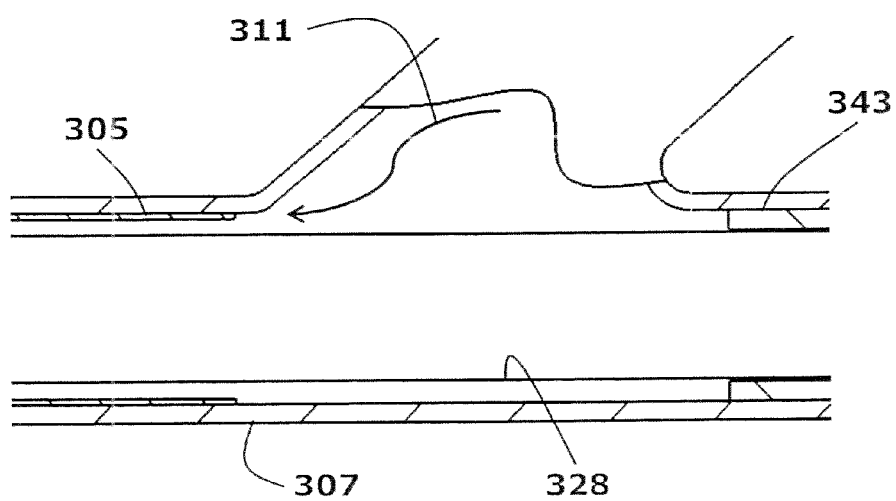
FIG. 53 is a cross-sectional side view of the area Z in FIG. 51.
Figure 54:
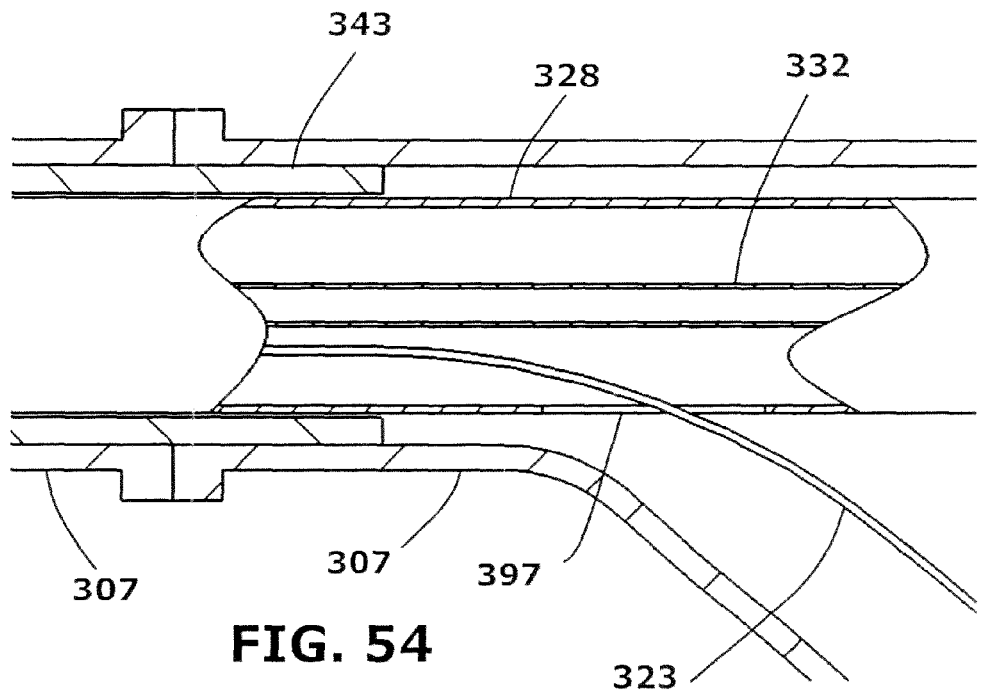
FIG. 54 is a cross-sectional side view of the area AA in FIG. 51.

The pull wire 323 is positioned within the catheter outer lumen 328 with one end 325 of the pull wire 323 permanently embedded within an airtight seal 336 serving as an anchor point. The pull wire 323 extends parallel with the delivery tube 332, and exits the wall of the catheter outer lumen 328 through an exit hole 397 (see FIG. 54), and then terminates at the steerable adjuster 329 that is mounted to the three-way connector 307. Referring to FIGS. 51 and 53, airtight seals 343, 395 together with the steerable adjuster 329, form a closed-airtight cavity to maintain vacuum integrity with the vacuum chamber 320.

This embodiment has the same outer profile as the embodiment of FIGS. 41-47, but is the most flexible of all the steerable catheters described herein due to the elimination of the holding tube 327. Positioning the angiogram outlet port 321 more proximally from the distal end 308 is preferred as the user can see the entire distal end 308 of the catheter as well as the state of blood vessel occlusion during treatment. This embodiment is a complete package and can be used independently without needing any additional guiding catheter or accessories as may be required by the non-steerable embodiments disclosed above.

Figure 57:
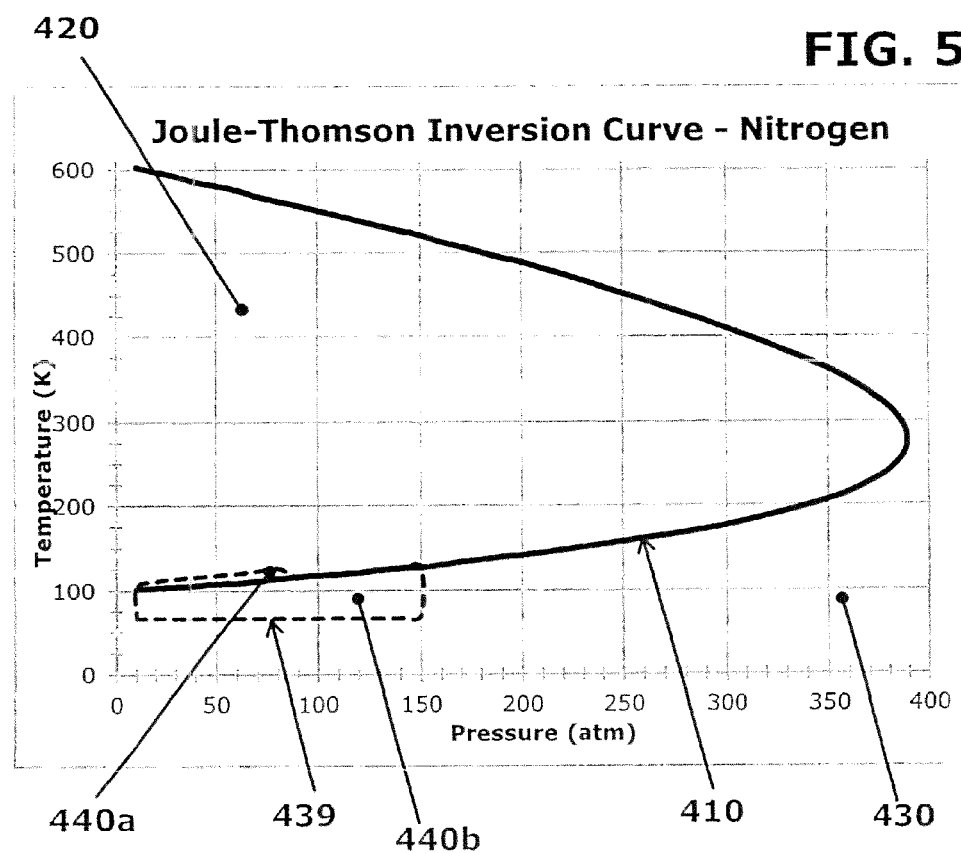
FIG. 57 illustrates an exemplary Joule-Thomson inversion Curve for the cryogenic fluid of the present invention.

The cryogenic fluid described herein is in a liquid phase. The cryogenic fluids of the present invention are designed to have its inlet operating temperature and pressure on its Joule-Thomson (J-T) Inversion Curve. FIG. 57 illustrates a J-T Inversion Curve 410 for the nitrogen gas of the present invention. The curve was generated from data provided by the National Institute of Standards and Technology (NIST) Chemistry WebBook. When a real fluid expands at a constant enthalpy or a J-T expansion, fluid temperature can increase, decrease, or remain constant depending on the initial temperature and pressure. A J-T Inversion Curve 410 separates the region where the fluid heats up 430 and cools down 420 during an expansion process. The J-T Inversion Curve is defined by two parameters, pressure, and temperature. The J-T Coefficient within the heating region 430 has a negative value and a positive value within the cooling region 420. Along the J-T Inversion Curve, the J-T Coefficient is zero. The J-T Coefficient is defined by the ratio of temperature change over pressure change at constant enthalpy. The cryogenic fluid of the present invention operates at a point on its J-T Inversion Curve wherein the J-T Coefficient can vary within 0.00±0.08 degrees F./atmosphere. The dashed lines 439 shown on FIG. 35 define the region 440 where the J-T Coefficient is within 0.00 ±0.08 degrees F./atmosphere. Region 440a defines the positive J-T Coefficient having values within the range of 0.00 to 0.08 degrees F./atmosphere. Region 440b defines the negative J-T Coefficient having values within the range of −0.08 to 0 degrees F./atmosphere.

The intention is to preserve the quality of the sub-cooled fluid transported to the catheter 102. This can be achieved by eliminating the effect of pressure changes due to fluid expansion/contraction along non-uniform flow passages leading to the catheter distal section 308 from the ablation system 106, in addition to other factors such as insulation. In the region away from the J-T Inversion Curve, pressure change results in temperature changes that alter the quality of the original fluid. By operating along the J-T Inversion Curve, constant fluid temperature can be supplied to the targeted area. The outcomes are controllable energy supply and predictable treatment level. Once the cryogenic fluid enters the catheter distal section 308, it absorbs heat from the surrounding, resulting in changes in fluid temperature, pressure, and phase. The degree to which these parameters change depends mostly on the thermal property of the surrounding tissue, the catheter construction and material, and cryogen flow rate, among others. The fluid exiting the catheter distal section 308 departs from the original operating point on the J-T Inversion Curve. It is not critical for the catheter return gas to operate on the J-T Inversion Curve. The function of the return gas is only for pre-cooling purposes.

The cryogenic fluid utilized is preferably liquid nitrogen. However, other cryogenic fluids may be utilized such as argon, neon, or helium. Liquid nitrogen contains very potent cold energy along with other properties making it an ideal fluid for cryoablation. It has high thermal capacity and fluid density, which means that it carries more cold energy in smaller volumes. As a result, liquid nitrogen can absorb a higher amount of heat energy for every degree change in its temperature as opposed to operating in other phases of nitrogen. With liquid nitrogen being a dense fluid, mass flow rate delivering to catheter distal end is possible through smaller tubing at a constant pressure. This allows for a more compact design. In addition to its specific heat energy (thermal capacity), liquid nitrogen also carries enthalpy heat energy. Enthalpy of vaporization or heat of evaporation of liquid nitrogen can further absorb heat while remaining at a constant temperature. Furthermore, liquid nitrogen has good thermal conductivity allowing absorbed heat to spread and dissipate efficiently.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A cryoablation system, comprising:
    a gas source which provides a working nitrogen gas at room temperature and at a constant set pressure;
    a liquid generator which is coupled to the gas source to receive the working gas, and which then generates a working cryogen fluid; and
    a catheter coupled to the liquid generator for receiving the working cryogen, the catheter having a distal section having a freezing element which delivers the working cryogen to a treatment location, and a flexible soft distal tip made from a biocompatible soft material that has a radiopaque characteristic, the catheter also having a balloon enclosing the freezing element, and an angiogram fluid delivery system;
    wherein the flexible soft distal tip is separate and distinct from the balloon and the enclosed freezing element, and the flexible soft distal tip has a smaller diameter than the diameter of the distal section;
    wherein the flexible soft distal tip is made of a material that is soft enough to alleviate damage caused to inner vessel walls during catheter insertion and removal; and
    wherein the biocompatible soft material is Pebax 2533 with 50% $BaSO_4$.

2. The system of claim 1, wherein the system further includes a vacuum system for providing a vacuum level to maintain proper thermal insulation to the cryogenic delivery lines against atmospheric heat, and wherein the catheter includes:
    an outer lumen;
    a vacuum chamber that is defined by the outer lumen of the catheter; and
    a pull wire, wherein the pull wire has a length, and a portion of the length of the pull wire is in communication with the vacuum chamber.

3. The system of claim 2, wherein the catheter includes an outer lumen, and a pull wire for steering, with the pull wire positioned within the outer lumen.

4. The system of claim 1, wherein the catheter includes an outer lumen, a balloon delivery tube that communicates with the interior of the balloon, and an angiogram fluid delivery tube that communicates with the vacuum chamber, and wherein a pull wire is positioned between the outer lumen and the balloon delivery tube.

5. The system of claim 4, wherein the distal section of the catheter includes a distal end, with an angiogram outlet port provided at the distal end.

6. The system of claim 4, wherein the catheter has an angiogram inlet port, and wherein the angiogram delivery tube is positioned within the outer lumen and extends from the distal end to the angiogram inlet port.

7. The system of claim 4, wherein the catheter includes a holding tube for holding the pull wire outside the outer lumen.

8. The system of claim 1, wherein the balloon is made from polyurethane, nylon, or PET.

9. The system of claim 1, wherein a spring wire is enclosed by the balloon, and couples the flexible soft distal tip and the freezing element.

* * * * *